United States Patent
Omori et al.

(10) Patent No.: US 6,609,135 B1
(45) Date of Patent: Aug. 19, 2003

(54) IMAGE FILE EQUIPMENT, AND DATABASE CREATING METHOD IN AN IMAGE FILE EQUIPMENT

(75) Inventors: Shinichi Omori, Hachioji (JP); Masakazu Omoto, Hachioji (JP); Kenichiro Nimoda, Hachioji (JP)

(73) Assignee: Olympus Optical Co., Ltd. (JP)

( * ) Notice: Subject to any disclaimer, the term of this patent is extended or adjusted under 35 U.S.C. 154(b) by 346 days.

(21) Appl. No.: 09/618,671

(22) Filed: Jul. 17, 2000

(30) Foreign Application Priority Data

Jul. 22, 1999 (JP) .......................................... 11-208140

(51) Int. Cl.[7] .............................................. G06F 17/30
(52) U.S. Cl. ........................ 707/104.1; 707/10; 705/3; 715/501.1; 715/515; 358/403
(58) Field of Search ................................. 358/403, 498; 705/3, 27; 707/104.1, 200, 2, 3, 4, 5, 7, 10; 715/501.1, 515

(56) References Cited

U.S. PATENT DOCUMENTS

| | | | |
|---|---|---|---|
| 5,111,306 A | | 5/1992 | Kanno et al. ............... 358/403 |
| 5,659,742 A | * | 8/1997 | Beattie et al. ........... 707/104.1 |
| 5,742,816 A | * | 4/1998 | Barr et al. ...................... 707/3 |
| 5,781,890 A | * | 7/1998 | Nematbakhsh et al. ........ 705/3 |
| 6,301,586 B1 | * | 10/2001 | Yang et al. .............. 707/104.1 |

FOREIGN PATENT DOCUMENTS

JP          4-987          1/1992

* cited by examiner

Primary Examiner—Jean M. Corrielus
Assistant Examiner—Shahid Alam
(74) Attorney, Agent, or Firm—Ostrolenk, Faber, Gerb & Soffen, LLP

(57) ABSTRACT

Image data is stored in any MO medium, and association information for associating image information in an MO medium with identification information for specifying the MO medium is managed by the respective image management tables of a plurality of image file apparatus. Each of the image file apparatus presents the identification information of an MO medium storing desired image data therein and thus makes a request for mounting the desired MO medium, thereby to obtain the desired image data. It is accordingly permitted to share image data among the plurality of image file apparatus.

22 Claims, 28 Drawing Sheets

FIG.2

13 PATIENT DATA TABLE

| PATIENT ID | NAME | SEX | DATE OF BIRTH | COMMENTS |
|---|---|---|---|---|
| 0001 | TARO △○ | M | 1973 02 19 | — |
| 0002 | HANAKO ◎△ | F | 1969 11 08 | — |
| ⋮ | ⋮ | ⋮ | ⋮ | ⋮ |

FIG.3

14 EXAMINATION DATA TABLE

| EXAMINATION ID | DATE OF EXAMINATION | PATIENT ID | BIOPSY | DEPARTMENT IN CHARGE | ... |
|---|---|---|---|---|---|
| 1240 | 1995 02 14 | 0001 | NOT MADE | FIRST SURGICAL DEPARTMENT | ... |
| 1241 | 1995 02 14 | 0002 | MADE | SECOND SURGICAL DEPARTMENT | ... |
| ⋮ | ⋮ | ⋮ | ⋮ | ⋮ | ⋮ |

PATIENT A ─┬─ 1995 02 14
           ├─ 1995 04 12
           └─ 1995 06 20

PATIENT B ─── 1995 03 20

IMAGE FILE EQUIPMENT, AND DATABASE CREATING METHOD IN AN IMAGE FILE EQUIPMENT

This application claims benefit of Japanese Application No. Hei 11-208140 filed in Japan on Jul. 22, 1999, the contents of which are incorporated by this reference.

BACKGROUND OF THE INVENTION

1. Field of the Invention

The present invention relates to an image file apparatus in which images are recorded and are searched for and restored, and also to a method of creating a database in an image file apparatus.

2. Prior Arc Statement

In recent years, endoscopes have been extensively used to observe a subject by inserting their elongate insertion portion into, for example, a body cavity. In general, the endoscopes are classified into fiberscopes which optically obtain the subject image, and electronic endoscopes which obtain an imaging signal correspondent to the subject image by an imaging device constructed of, for example, a CCD (charge-coupled device) attached to the distal end of the insertion portion. A fiberscope can also generate an imaging signal correspondent to the subject if an external imaging device is attached thereto. When the endoscope furnished with the imaging device in this manner is used, the obtained image can be electronically recorded, and the electronic recording is easier to manage and the image data is easier to edit compared to photographing and recording the optical image on a film. Therefore, it is a recent trend to electronically record endoscopic images. Also in, for example, the field of cameras, digital cameras, in which a subject image is picked up by a built-in imaging device to electronically record the image, have come into wide use instead of conventional cameras.

In recording images in an endoscope, the imaging signal is converted into a digital video signal, for which a digital recording medium, for example, a hard disk (HDD), a magnetooptic disk (MO) or a digital video disk (DVD), can be employed. Accordingly, image file apparatus has been used for recording image data generated by an endoscope unit in the digital recording medium for retention and management, such as searching and retrieval.

In general, the image file apparatus for recording the image data of the endoscopic image etc. as mentioned above includes an image inputting unit, an image recording unit, and an image reproducing unit. With such an image file apparatus, in the case of an endoscopic examination by way of example, the patient's ID, name, date of birth, sex, etc. are inputted as data using a keyboard or the like input means connected to the endoscope unit. The inputted patient data are recorded along with the endoscooic image generated in the endoscopic examination. After the examination, the recorded image can be reproduced by searching the data, for example, the recorded patient data or examination data, such as the date of examination, as a search key. In addition, other information relating to the examination can be inputted and retained as the examination data. Accordingly, the utilization of the image file apparatus permits, for example, for searching and display of an image in the past examination of an identical patient, to observe the change of the affected part or the like, in order to efficiently make a diagnosis and perform a medical treatment.

Such image file apparatus includes a plurality of image file apparatus interconnected in a network, and a stand-alone image file type which can input, record, and search for and display an image alone.

Since the plurality of image file apparatus are interconnected by a network, the respective image file apparatus of the network type can access an identical database or recording medium, and the image data and various other data that are shared among all the image file apparatus. Accordingly, when data has been added or updated in accordance with the newest input information from any of the image file apparatus, any of the image file apparatus can utilize the data. With the image file apparatus of the network type, however, a large-scale system is inevitable because, for example, a network cable and units such as a communication unit, and installation spaces therefor are required. Another disadvantage is that facilities of comparatively small scale having a small number of examination beds have difficulty using an image file apparatus of the network type, because it is bulky and expensive to install.

On the other hand, since the image file apparatus of the stand-alone type does not require the units and installations to make a network it is comparatively less expensive, and the apparatus of this type can be easily introduced into the facilities of small scale having, for example, only one examination bed. Besides, in facilities of medium scale where the introduction of the network type image file apparatus of large scale is unnecessary, but where one stand-alone type image file apparatus is insufficient, an operational control employing a plurality of stand-alone type image file apparatus is desirable. That is, the image file apparatus of the stand-alone type has the advantage of a high flexibility for the scale of the introducing facilities.

However, in the environment where the plurality of image file apparatus of the stand-alone type are used, the data such as image data cannot be shared among the image file apparatus unlike those in the image file apparatus of the network type, and the data recorded in a certain image file apparatus cannot be accessed by another image file apparatus. In this manner, the plurality of image file apparatus of the stand-alone type have the disadvantage of inferior operability.

OBJECTS AND SUMMARY OF THE INVENTION

An object of the present invention is to provide an image file apparatus and a database creating method in an image file apparatus, in which, when a plurality of image file apparatus are used without being connected to a network, data are permitted to be shared among all the image file apparatus.

Another object of the present invention is to provide an image file apparatus and a database creating method in an image file apparatus, in which a database management is realized by associating identification information unique to a recording medium such as an MO medium, with patient data and examination data.

Still another object of the present invention is to provide an image file apparatus and a database creating method in an image file apparatus, in which a recording medium required in the case of displaying an image can be quickly specified by making a search on the basis of a piece of information such as patient data or examination data, thereby presenting the desired image display, and simultaneously, the patient data, the examination data or the like for aiding the diagnosis of a patient, explaining the result of the examination to the patient, and so forth.

Yet another object of the present invention is to provide an image file apparatus and a database creating method in an image file apparatus, in which, patient data or examination data, can be quickly searched by inputting only the identification information of a patient, when the data for the pertinent patient have already been registered.

An image file apparatus according to the present invention comprises recording medium mount means for exchangeably mounting a first recording medium on which first image information can be recorded; image-information record means for recording the first image information on the first recording medium which can be mounted in said recording-medium mount means; managing-data creation means for creating first managing data for said image information which is recorded on said recording medium by said image-information record means; database means for storing therein the first managing data which is created by said managing-data creation means; and database additional-storage means for additionally storing second managing data for second image information which is recorded on a second recording medium in said database means when the second recording medium on which the second image information not managed by said database means is recorded is mounted in said recording-medium mount means.

An image file system according to the present invention comprises a first image file apparatus which is provided with first recording-medium mount means for exchangeably mounting a first recording medium capable of recording first image information thereon; first image-information record means provided in said first image file apparatus for recording the first image information on the first recording medium that is mountable in said first recording-medium mount means; first managing-data creation means provided in said first image file apparatus for creating first managing data for said first image information that is recorded on said first recording medium by said first image-information record means; managing-data record means provided in said first image file apparatus for recording on said first recording medium the first managing data that is created by said first managing-data creation means; a second image file apparatus provided with second recording-medium mount means for exchangeably mounting a second recording medium capable of recording second image information thereon; second image-information record means, provided in said second image file apparatus, for recording the second image information on the second recording medium that can be mounted in said second recording-medium mount means; second managing-data creation means provided in said second image file apparatus for creating second managing data for said second image information that is recorded on said second recording medium by said second image-information record means; database means provided in said second image file apparatus for storing therein the second managing data that is created by said second managing-data creation means, and database additional-storage means provided in said second image file apparatus for additionally storing the first managing data recorded on the first recording medium in said database means when said first recording medium, on which the first image information is recorded in said first image file apparatus, is mounted in said second recording-medium mount means.

A database creating method in an image file apparatus according to the present invention comprises the first image-information record step of recording an image information on a first recording medium which can be mounted in a recording-medium mount means by an image-information record means; a managing-data creation step of creating first managing data for the first image information that is recorded on the first recording medium by the first image-information record means; a database storage step of storing the first managing data that is created by said managing-data creation step in the database means, and a database additional-storage step of additionally storing second managing data for the second image information that is recorded on a second recording medium in the database means when the recording medium, on which the second image information not managed by said database means is recorded, is mounted in the second recording-medium mount means.

Other features and advantages of the present invention will be satisfactorily clarified from the ensuing description.

BRIEF DESCRIPTION OF THE DRAWINGS

FIG. 2 is an explanatory diagram showing the data layout of a patient data table;

FIG. 3 is an explanatory diagram showing the data layout of an examination data table;

DETAILED DESCRIPTION OF THE PREFERRED EMBODIMENTS

Figure 1:
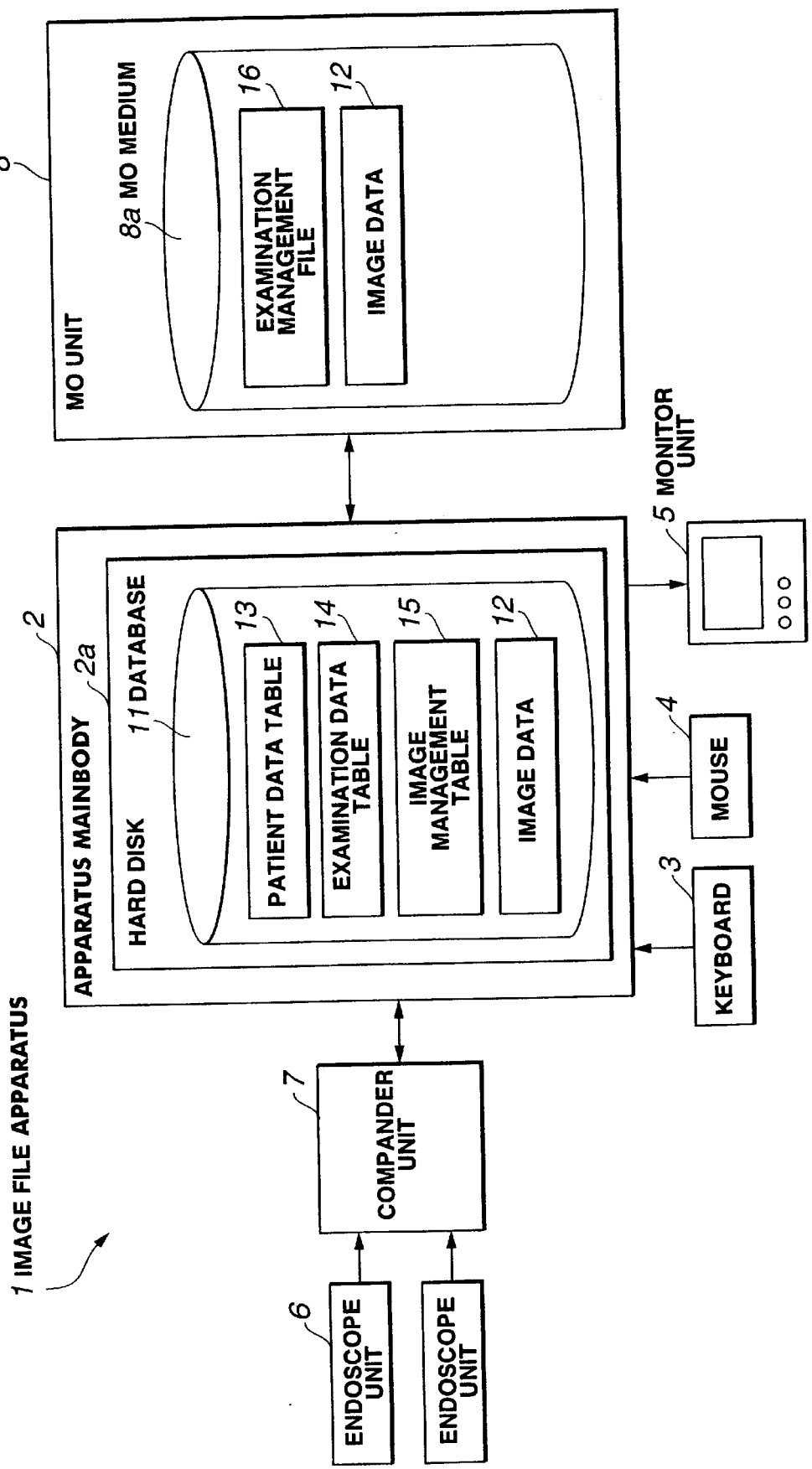
FIG. 1 is a block diagram showing the construction of an image file apparatus.

As shown in FIG. 1, an image file apparatus 1 in this embodiment retains medical service information items including endoscopic images. The image file apparatus 1 comprises the apparatus main body 2, which controls the various portions of this image file apparatus 1, a keyboard 3 and a mouse 4 which are connected to the apparatus main body 2 and with which operating instructions and data are inputted, a monitor unit 5, which is connected to the apparatus main body 2 and on which operating screens and the medical service information items including endoscopic images are displayed, a printer (not shown) which is connected to the apparatus main body 2 as needed and which prints the medical service information items including endoscopic images, a compander unit 7 which is connected to the apparatus main body 2 and which compresses image data inputted from an endoscope unit 6 and then delivers the compressed data to the apparatus main body 2, or which expands image data in compliance with a command from the apparatus main body 2, and an MO unit 8 in which data are recorded.

The apparatus main body 2 is constructed on the basis of, for example, a personal computer, and it includes therein, at least, a storage means such as a hard disk 2a which stores data in a database 11. The apparatus main body 2 can have a plurality of MO units 8 connected thereto.

Two endoscope units 6, for example, are connectible to the compander unit 7. By way of example, each of the endoscope units 6 is constructed having an electronic endoscope, which is inserted into, e.g., a body cavity for obtaining image signals from a subject image, and a video processor performing processing on imaging signal obtained by the electronic endoscope and feeding the compander unit 7 with a video signal including an endoscopic image, though the construction is omitted from illustration. The endoscope unit 6 is made from components not shown, for example, an elongate insertion portion which is inserted into, for example, the body cavity, an operation portion, which is joined to the base end side of the insertion portion, an imaging device, which is built on the distal end of the insertion portion, for picking up the subject image in order to generate the imaging signal, and a release switch, which is disposed in the operation portion, and with which the instruction of releasing an image, namely, the instruction of recording an image is inputted. When the release switch is manipulated, a release signal is fed to the compander unit 7 and the apparatus main body 2 to trigger image recording. If necessary, the video processor is furnished with a keyboard not shown, with which patient information is inputted. The patient information is sent to the apparatus main body 2 through the compander unit 7. Incidentally, the invention is not restricted to endoscope unit 6. The endoscopic unit 6 may as well be replaced with any other observation unit for obtaining medical images, for example, an ultrasonic diagnostic unit.

The database 11 stores, for example, image data 12, which consist of endoscopic image information, a patient data table 13, which contains patient information, an examination data table 14, which contains examination information, and an image management table 15, which contains information for managing the image data.

The image data 12 and an examination management file 16, for example, are stored in an MO medium 8a, which is an external storage medium installed in the MO unit 8. Herein, the examination management file 16 contains a storage medium ID, which is the identification information for specifying the MO medium 8a, and patient information and examination information, which concern the image data 12 stored in the MO medium 8a. Incidentally, the MO unit 8 may be replaced with any other digital recording unit, for example, a removable hard disk unit or a digital video disk.

The storage medium ID of the MO medium 8a is the identification information that is unique to each individual MO medium 8a, and is written during, for example, the formatting operation of the MO medium 8a. In addition, the image file apparatus 1 is adapted to specify the MO media 8a in accordance with the storage medium IDs. The storage medium IDs are unique to the individual MO media 8a, when, for example, searching for and displaying the desired one of the image data 12, the user of the image file apparatus 1 can obtain the desired image data 12 by specifying the storage medium ID of the MO medium 8a in which the desired image data 12 is stored, and then making a request for mounting in the MO unit 8 the MO medium 8a that bears the specified storage medium ID.

The storage medium ID is expressed by the combination of, for example, a facilities ID, which is unique to facilities where the image file apparatus 1 is mounted, an apparatus ID, which specifies each image file apparatus 1 within the identical facilities, and format No., which increments each time the MO medium 8a is formatted in the identical image file apparatus 1. In this embodiment, the facilities IDs are IDs that are unique to the individual facilities and which may also be, for example, the serial numbers of the apparatus main body 2 or software installed in the apparatus main body 2. The apparatus IDs are nursers which are unique to the image file apparatus 1. Where a plurality of image file apparatus 1 are used in the identical facilities, serial numbers that increment every time the number of the image file apparatus 1 as, "01", "02", "03", . . . , "N" (N being a natural number), . . . can be the apparatus IDs. Accordingly, the MO medium 8a formatted for the first time is provided with the storage medium ID of, for example, "ABCD0123 01 000001" which would indicate that the apparatus ID of the image file apparatus 1 is "01", and the facilities ID of the file apparatus 1 is "ABCD0123".

As shown in FIG. 2, the patient information items of respective examined patients are recorded in the patient data table 13, as one record for each patient. The patient data table 13 contains the patient information items, for example, "Patient ID", which is a No. separately allotted to every patient so as to identify each patient, "Name", "Sex and "Date of Birth". Any patient, therefore, can be specified by the patient information items.

As shown in FIG. 3, information items relevant to examinations are recorded in the examination data table 14, with one record composed of information corresponding to each examination. The examination data table 14 contains the examination information items, for example, "Examination ID", which is a No. given in the order of the examinations made, "Date of Examination", "Patient ID", information indicative of the presence or absence of a biopsy, and "Department in charge" where the examination was made. Any examination, therefore, can be specified by the examination information items. Apart from the examination information items indicated in the figure, the examination data table 14 may contain, if required, examination information items, for example, "Age at Examination", "Comments on Examination", "Sort of Examination", "Distinction of Inpatient/Outpatient", "Type of Endoscope", "Examining Doctor", "Diseased Part", "Diagnosed Disease Name", "Biopsy No.", "Details of Diagnosis", "Bioptic Results", "Special Examination", "Sort of Film", "Film No." and "Film Location".

Figures 4, 5:
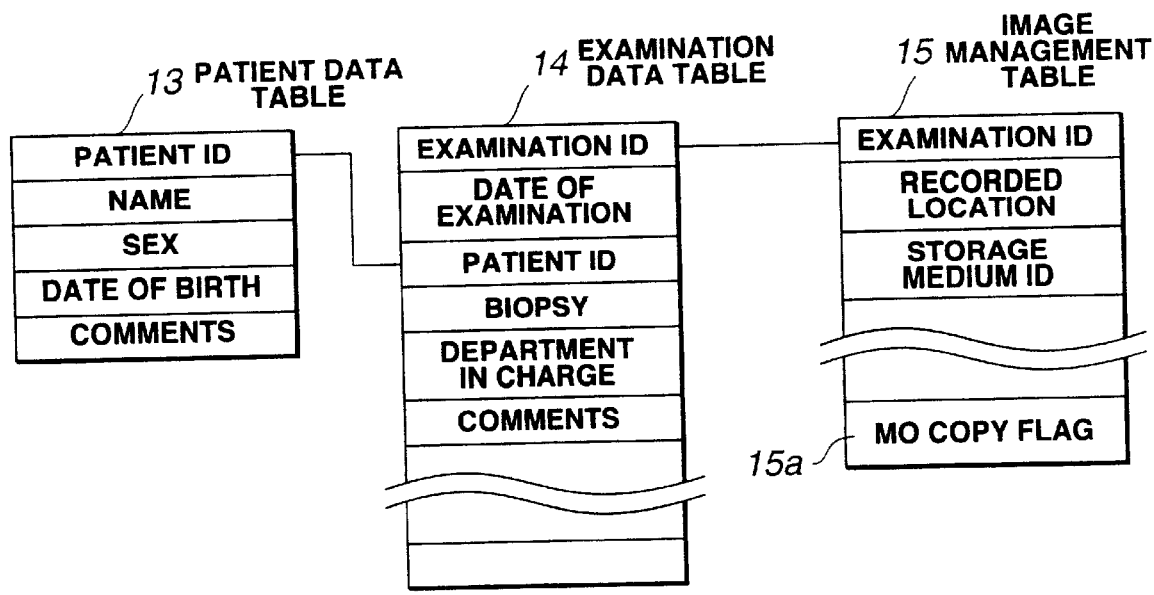
FIG. 4 is an explanatory diagram showing the relationship between patients and examinations.
FIG. 5 is an explanatory diagram showing the relationship among the patient data table, the examination data table and an image management table.

As shown in FIG. 4, an examination is sometimes made only once for one patient as in the case of a patient B, but examinations are often made a plurality of times for one patient as in the case of a patient A because of periodical examinations, successive examinations, a reexamination, different kinds of examinations, etc. As shown in FIG. 5, therefore, the patient data table 13 and the examination data table 14 are associated using patient IDs as keys, and a plurality of examination information items for each patient are recorded in association with each other. In addition, the examination data table 14 and the image management table is are associated using examination IDs as keys. In this manner, the patient data table 13, examination data table 14 and image management table 15 are linked to build a relational database, so that the desired information including image data can be searched using one piece of information. For each examination data item, the image management table 15, the examination ID related with the examination data table 14, the recorded location of the image data 12, a storage medium ID for specifying the MO medium 8a storing the image data 12 therein, and an MO copy flag 15a indicating whether or not the image data 12 has been copied from the hard disk 2a into the MO medium 8a. Incidentally, the image data 12 obtained with the image file apparatus 1 is copied into any MO medium 8a.

Figure 6:
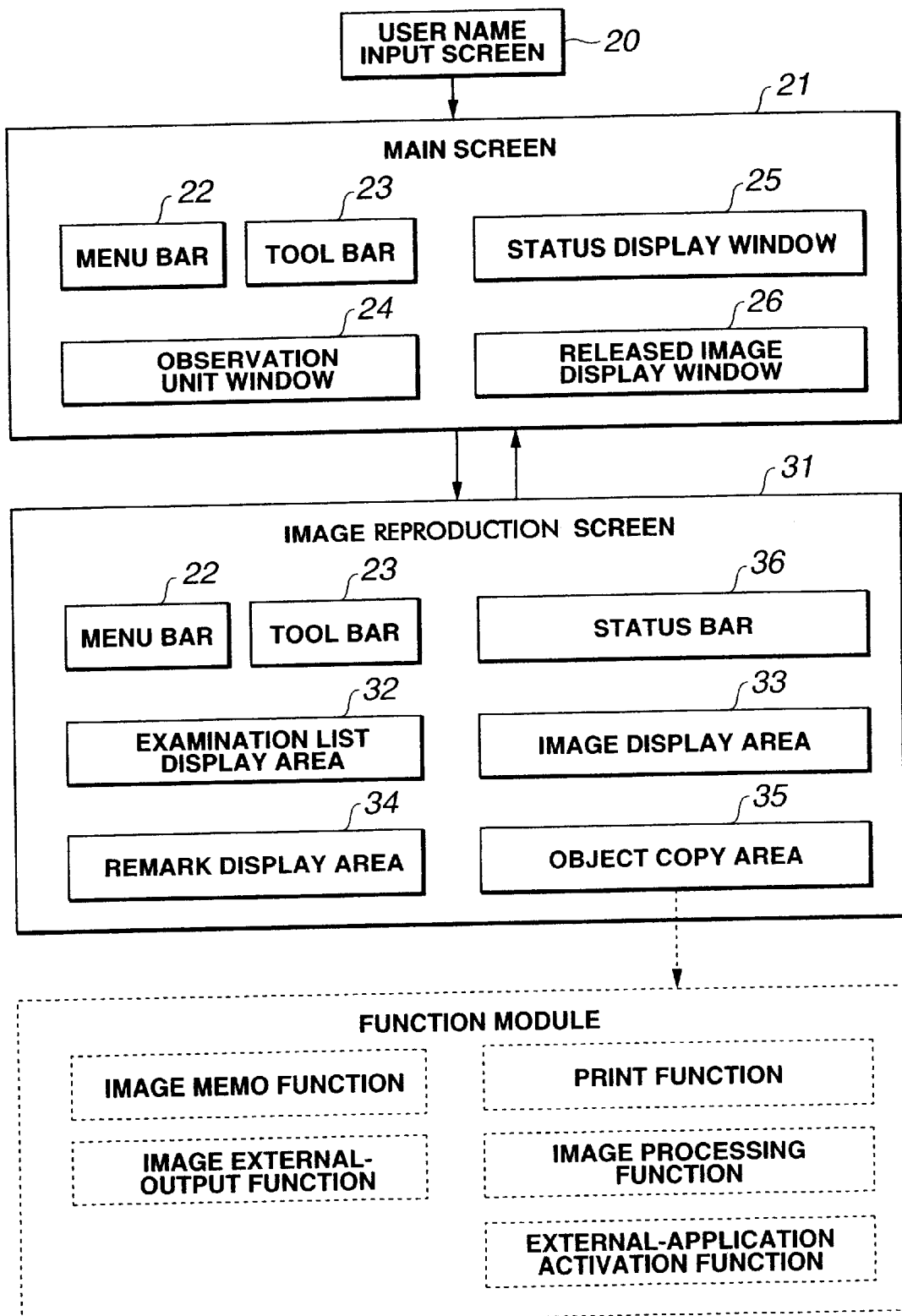
FIG. 6 is a screen transition diagram showing the relationship among a user name input screen, a main screen and an image reproduction window screen.

As shown in FIG. 6, operating screens, which are displayed on the monitor unit 5 of the image file apparatus 1, are broadly classified into a user name input screen 20 that corresponds to the function of authenticating a user, a main screen 21, which is displayed transitively from t he user name input screen 20 and which corresponds chiefly to the function of recording data such as image data, is generated by an examination such as endoscopic examination , and an image reproduction screen 31, which is displayed alternately with the main screen 21 and corresponds chiefly to the function of searching for and reproducing the image data or the like.

The user name input screen 20 appears when the power supply of the image file apparatus 1 is turned ON, and it requests the user to enter a user name and a password as inputs. Here, when the appropriate user name and password is entered the user is authenticated, and the main screen 21 is activated. Unless an appropriate user name and password are entered into the user name input screen 20, the main screen 21 cannot be activated. Thus, the image file apparatus 1 is protected from the unauthorized use thereof and the destruction of data by an unauthorized user. In addition, the detailed operational control of user levels can be performed in such a way that the ranges of utilizable functions, the ranges of accessible data, and the ranges of authorization to record and update data are set depending upon users.

Figure 7:
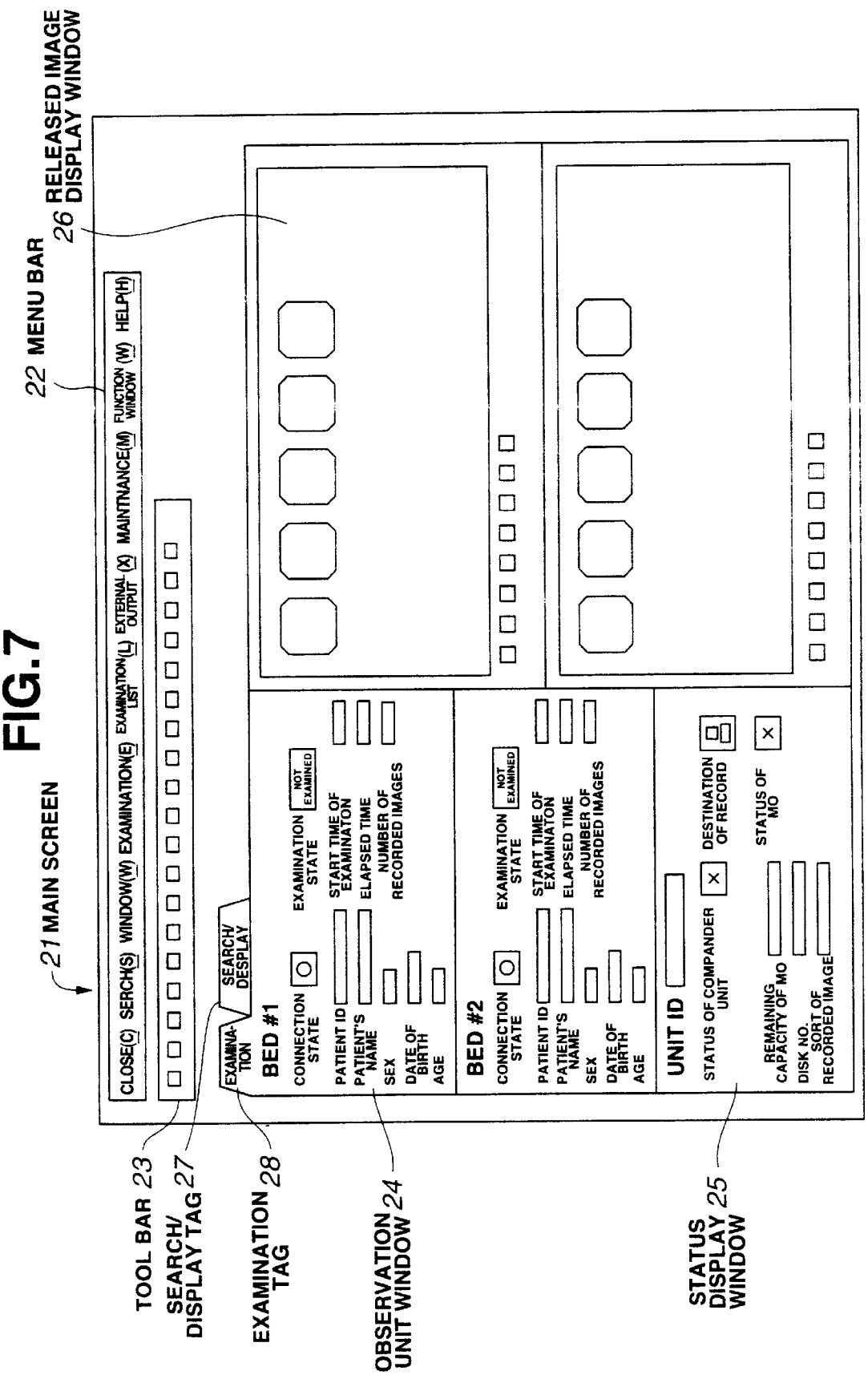
FIG. 7 is an explanatory diagram showing a display example of the main screen.

As shown in FIG. 7, the main screen 21 is formed chiefly having a menu bar 22, a tool bar 23, an observation unit window 24, a status display window 25 and a released image display window 26. These areas have respectively independent functions as so-called windows. In addition, the main screen 21 is provided wits a search/display tag 27 and a n examination tag 28 for providing the instruction for changing the screen to the image reproduction screen 31.

The menu bar 22 i s an operation guidance display for invoking any of the functions prepared in the image file apparatus 1 through menu selection, while the tool bar 23 is a group of icons for invoking any of the functions prepared in the image file apparatus 1 through a mouse click operation by way of example. With the menu bar 22 and the tool bar 23, it is possible to invoke the functions, for example, the termination of the image file apparatus 1, the execution of a data search, the retention of inputted data, and maintenance of data.

Displayed in the observation unit window 24 are the executional situations of the observation units connected, such as endoscope units 6, at most two of which are connected, and the patient data of patients who are under examinations with the observation units.

Displayed in the released image display window 26 are the images generated by the examinations with the endoscope unit 6 in the order of releases and on a reduced scale, in correspondence with the respective endoscope unit 6 connected which are at most two.

The statuses of the image file apparatus 1 are displayed in the status display window 25. Information items that indicate the statuses of the image file apparatus 1 are, for example, the status of the compander unit 7, the status of the MO unit 8, the recording destination of the obtained images, the storage medium ID of the MO medium 8a (written as "Disk No." in the figure), and the remaining capacity of the MO medium 8a. Thus, it is possible to check the connection states and operation states of the units which constitute the image file apparatus 1.

When the search/display tag 27 which is in the upper part of the main screen 21, is clicked with the mouse 4, the main screen 21 is transited to the image reproduction screen 31, which corresponds to the function of searching for and displaying data. To the contrary, when the examination tag 28 is clicked with the mouse 4 during the display of the image reproduction screen 31, this screen 31 is transited to the main screen 21, which corresponds to the function of recording image data generated by the endosconic examinations. By the way, the search/display tag 27 and the examination tag 28 are omitted from illustration in FIG. 9 et seq.

Now, the operations during the endoscopic examination of the main screen 21 will be described.

First, at the beginning of the examination, patient data are inputted from the observation unit such as endoscope unit 6. Then, the inputted patient data are transmitted to the side of the image file apparatus 1 and are displayed in the observation unit window 24. The patient data may also be inputted from the keyboard 3 of the image file apparatus 1, rather than the observation unit. In such an event, the data inputted from the keyboard 3 are also transferred from the image file apparatus 1 to the observation unit if needed. In addition, where the examination for the patient has been made before and if the pertinent patient data have already been registered in the database 11, only the patient ID needs to be inputted so that the patient data table 13 of the database 11 is searched for the pertinent patient data, which are automatically displayed.

Subsequently, when the examination with the endoscope unit 6 is started, endoscopic images are successively recorded in the image file apparatus 1 in compliance with release commands from the endoscope unit 6. The recorded images are reduced and displayed in the released image display window 26. Thus, the user can know the situation of the examination on the main screen 21.

Also, when the examination is started, the start time of the examination, an elapsed time since the start of the examination and the number of recorded images are displayed in the observation unit window 24. Thus, the user can know the status of the examination. Here, the start time of the examination, that is, the time at which such data as the patient data are registered in the image file apparatus 1, may also be set at, for example, the point of time at which the first image has been released to start the recording of the image data. In addition, the start time of the examination may also be set when the instruction for starting the examination has been given from the keyboard 3 or the mouse 4. In such a case, the start time of the examination can be precisely recorded. Moreover, it is not restrictive to give the instruction of the start of the examination from the keyboard 3 or the mouse 4 of the image file apparatus 1. The function of giving the instruction of the start of the examination may as well be allotted to, for example, a predetermined switch of the endoscope unit 6 so that the apparatus main body 2 receives a signal from the switch through communications.

The image data commanded to be released by the endoscope unit 6 are recorded in the hard disk 2a of the image file apparatus 1, and are copied from the hard disk 2a into the MO medium 8a mounted in the MO unit 8. In this state, whether the MO medium 8a is mounted in the MO unit 8 and whether the remaining capacity of the MO medium 8a mounted in the MO unit 8 is sufficient are known from the displayed contents of the status display window 25. In addition, where the MO medium 8a is not inserted in the MO unit 8 or where the remaining capacity of the MO medium 8a is insufficient, the data are recorded in only the hard disk 2a.

Here, whether or not the data have been copied from the hard disk 2a into the MO medium 8a is managed by the MO copy flag 15a of the image management table 15 (refer to FIG. 5). Where the data not copied yet exist in the hard disk 2a, the data are copied from the hard disk 2a into the MO medium 8a when the MO medium 8a has been inserted into the MO unit 8 anew. In this manner, the status of the completion/incompletion of the data copying from the hard disk 2a into the MO medium 8a is managed by the MO copy flag 15a. Therefore, even when the user has forgotten to insert the MO medium 8a or when the remaining capacity of the MO medium 8a is insufficient, the recording of the image can be continued without interrupting the examination.

Moreover, the examination is not interrupted even when release commands are frequently issued due to the simultaneous connection of the two endoscope units 6 to the image file apparatus 1, and where the MO unit 8 of low recording speed fails to record the image incidentally, the data copying from the hard disk 2a into the MO medium 8a does not have to proceed substantially concurrently with the recording of the data in the hard disk 2a. Such data may as well be collectively copied when the image file apparatus 1 has been started or ended operating or when the operator has manually given the instruction of copying.

In addition, in making the examination or during the examination, it is permitted to determine whether the units are normally operating, whether the remaining capacity of the MO medium 8a poses a problem, etc., by observing the display of the status display window 25.

A series of examining steps are executed in the above way. In ending the examination, an unshown "examination end button", which is provided in the endoscope unit 6, is manipulated, for which the examination is ended. When the end of the examination is thus instructed, the patient data and released images relevant to the endoscope unit 6 are cleared. Incidentally, the instruction of ending the examination is not issued only from the endoscope unit 6, but it may also be given through the operation of the keyboard 3 or mouse 4 of the image file apparatus 1. In such an event, a signal notifying the end of the examination is sent from the side of the image file apparatus 1 to the side of the endoscope unit 6.

Figure 8:
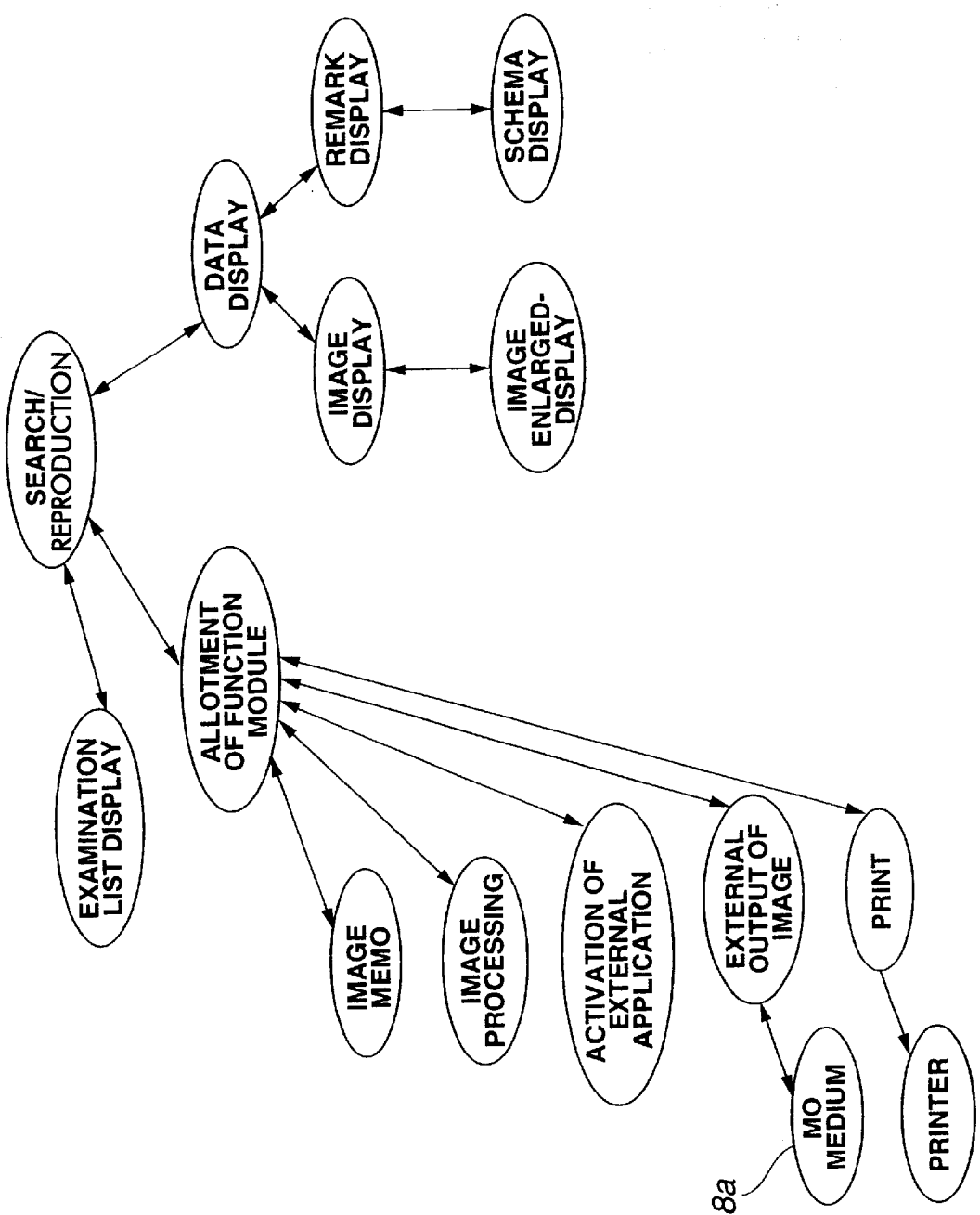
FIG. 8 is an explanatory diagram showing a functional configuration relevant to the image reproduction screen.

Next, in order to describe the organization of the image reproduction screen 31, the functional configuration of the data search/display function based on the image reproduction screen 31 will be outlined beforehand with reference to FIG. 8. As shown in the figure, the data search/display function is configured chiefly having the examination list display function of displaying the list of examinations, the data display function of reproducing and displaying recorded data, and the functional-module allotment function of delivering the recorded data, such as image data, to various functional modules. The data display function is configured to have the image display function of displaying the image data, and the remark display function of displaying remark data. The image display function is configured to have the image enlarged-display function of enlarging an index image displayed on a reduced scale, and displaying the enlarged image. The remark display function is configured to have the schema display function of displaying in association with the parts of a living body on a graphic display—which schematically illustrates the viscus of the living body and is called a "schema display" for the sake of convenience—and remark data corresponding to the body parts.

The functional modules to which the data are delivered by the functional-module allotment function are, for example, the image memo function of temporarily retaining the selected image data or remark data in a predetermined folder within the hard disk 2a, the image external-output function of converting the image data into a preappointed data format (such as bitmap format or JPEG format) as needed and copying the image data into an external record medium such as the MO medium 8a, the print function of outputting the selected image data to the printer after the preview display thereof or outputting the remark data to the printer, the image processing function of submitting the selected image data to predetermined image processing and then displaying the processed data, and the external-application activation function of activating an external application and then delivering the image data or remark data to the external application. The "external application" signifies application software such as word processor software, table and calculation software, slide creation software or an editor, which is generally available on the market and which is installed in the image file apparatus 1 beforehand.

Figure 9:
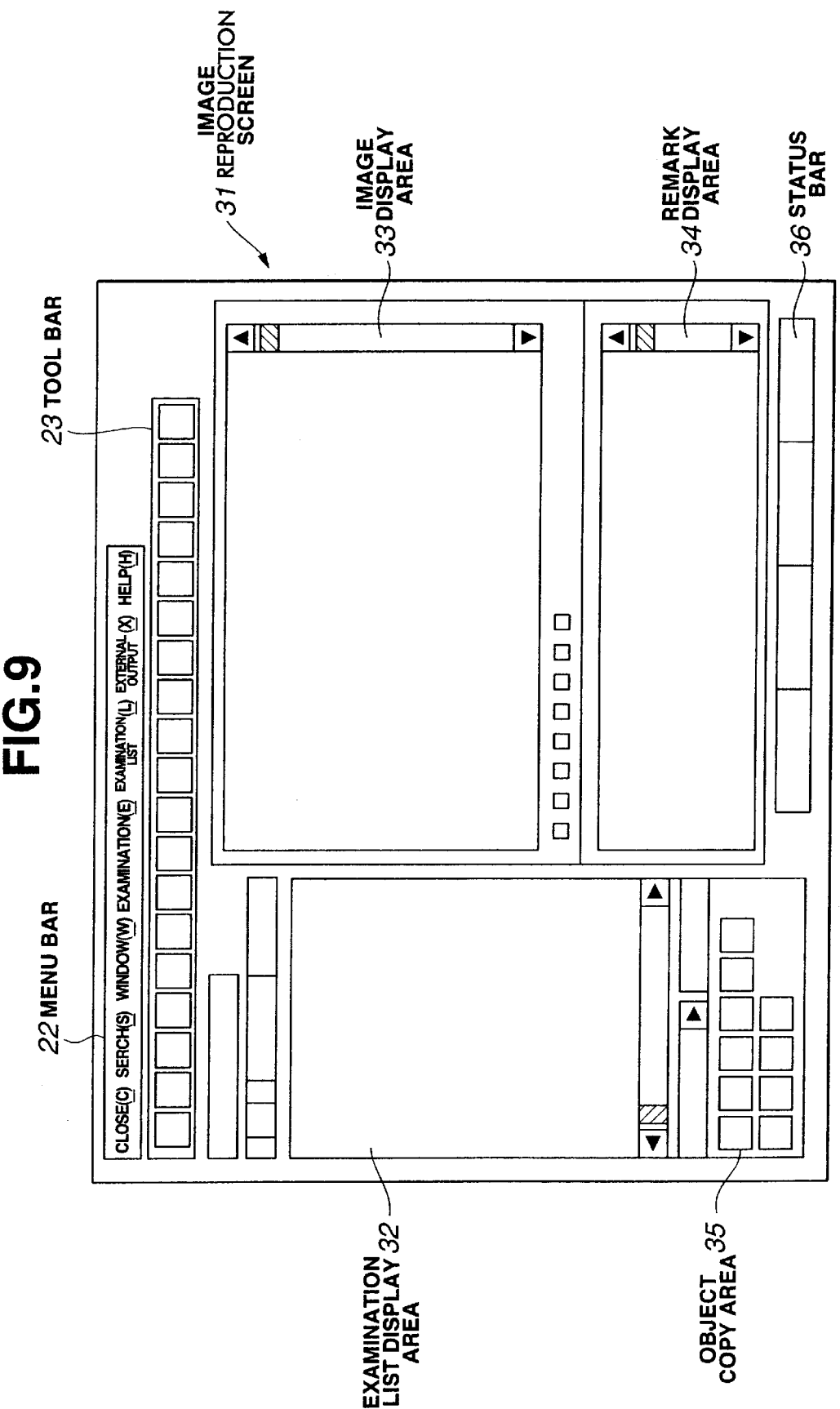
FIG. 9 is an explanatory diagram showing the organization of the image reproduction screen.

Next, the organization of the image reproduction screen 31 will be described with reference to FIGS. 6 and 9. The image reproduction screen 31 is formed chiefly having the menu bar 22 as well as the tool bar 23, an examination list display area 32, an image display area 33, a remark display area 34, an object copy area 35 and a status bar 36. The roles of the areas will be explained below. Incidentally, the respective areas have independent functions as so-called "windows".

The menu bar 22 and the tool bar 23 contain the menu items of functions prepared in the image file apparatus 1, or iconized menu items. Here, it is possible to utilize the functions of closing the screen 31, namely, ending the operation of the image file apparatus 1, executing a search, altering a display layout, retaining inputted remark data, customizing predetermined menu items, and so forth. Incidentally, the functions prepared in the menu bars 22 and the tool bars 23 of the main screen 21 and the image reproduction screen 31 may as well be made different in accordance with the screen functions of the respective screens.

The examination list display area 32 corresponds substantially to the examination list display function shown in FIG. 8, and it is an area where the search conditions of an examination are selected and set, and where the results of a search are displayed as a list.

The image display area 33 corresponds substantially to the image display function shown in FIG. 8, and it is an area where the index images of the image searched for are displayed.

The remark display area 34 corresponds substantially to the remark display function shown in FIG. 8, and it is an area where the remark information of the examination is displayed. Besides, data can be inputted to the remark display area 34, and the data inputted here are recorded in image record means, for example, the hard disk 2a, in association with the image data. The inputted data can also be used as a keyword for searching of the image data.

The object copy area 35 corresponds substantially to the functional-module allotment function shown in FIG. 8, and it is an area where the image data or/and the remark data are delivered to any of the functional modules prepared. The respective functional modules are iconized, and the instruction of delivering the data to the corresponding functional module and executing the corresponding function can be given by the dragging and dropping of the image data or remark data onto the corresponding icon.

The status bar 36 is an area which displays the processing situation of any of the units, the number of examinations hit by the search, the number of images, and so forth.

Figure 10:
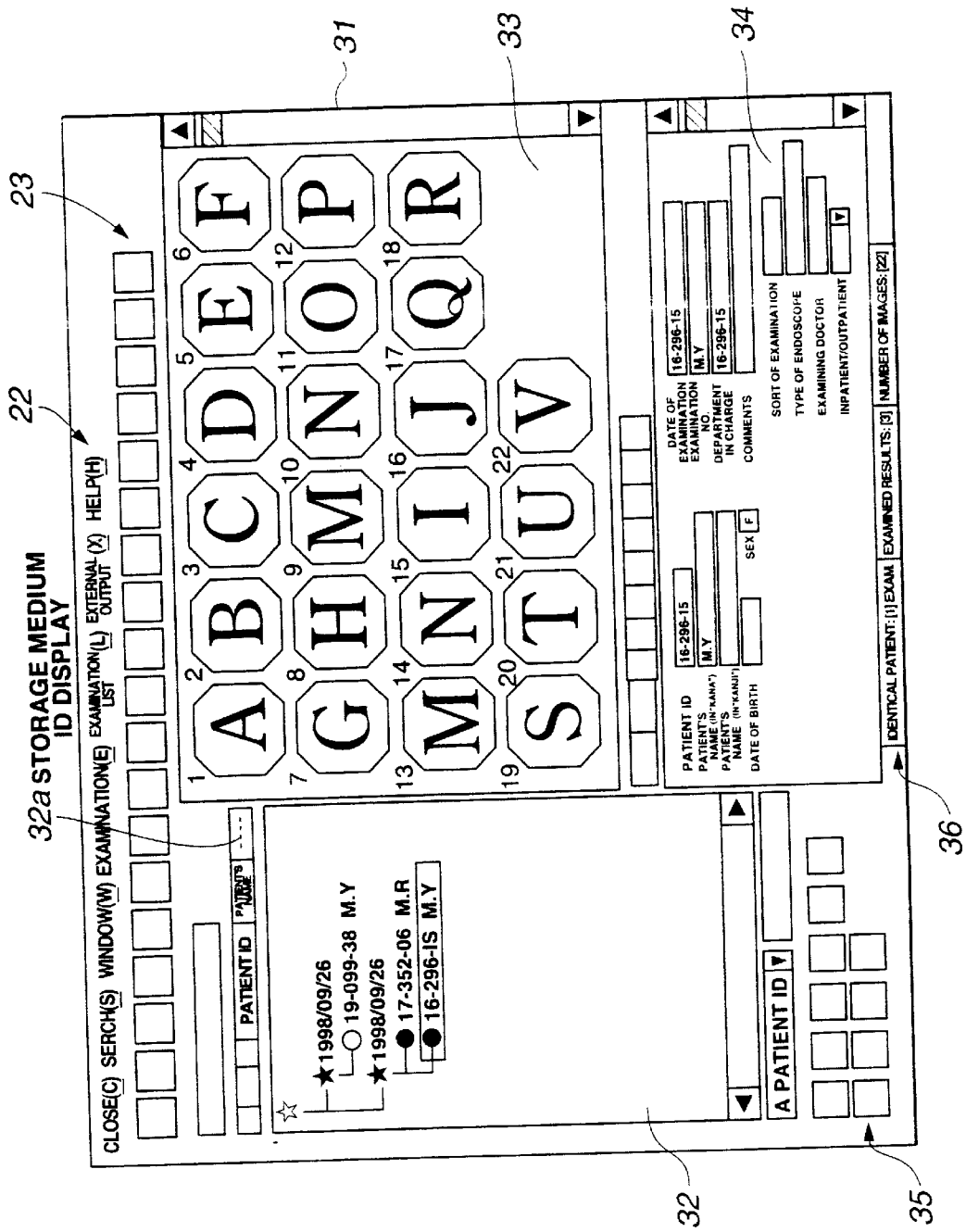
FIG. 10 is an explanatory diagram showing a display example of the image reproduction screen.

As shown in FIG. 10, when a search is performed by designating a keyword or the like in the image reproduction screen 31, the index images of a group of searched for images are displayed on the image display area 33.

Figure 11:
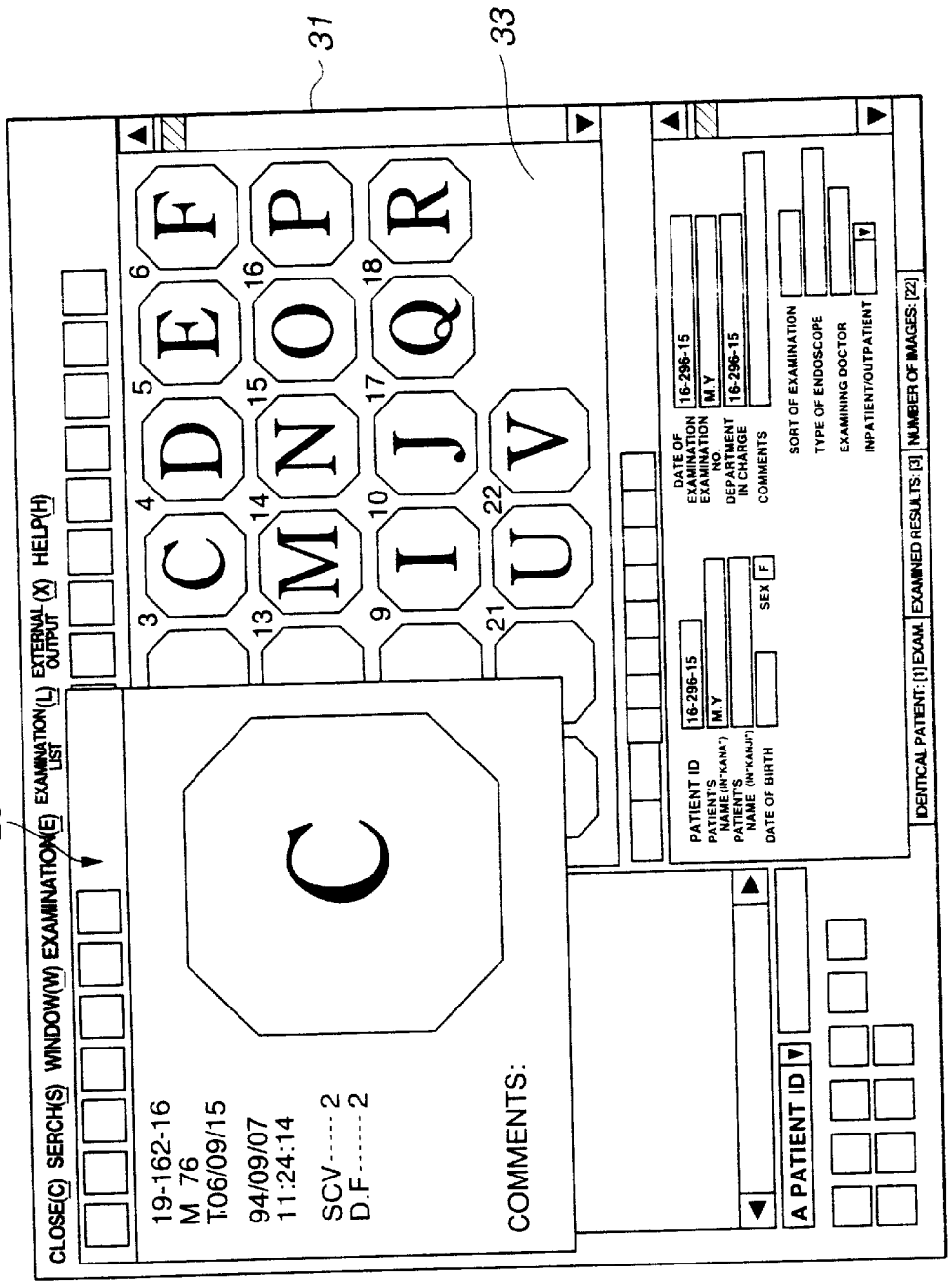
FIG. 11 is an explanatory diagram showing an example of an image display on the image reproduction screen.

FIG. 11 shows the result obtained when one of the index images displayed on the image display area 33 in FIG. 10 is designated to display the index image with an original image size on the image reproduction screen 31. The designation can be done by double-clicking the index image.

As shown in FIG. 11, a plurality of iconized buttons for functions which can be executed for the image of the original image size are provided over the image of the original image size. Only the original image can be submitted to the enlarged or reduced display thereof on the monitor unit 5, the print thereof by the printer, the retention thereof in the hard disk 2a within the image file apparatus 1 (the copying thereof into a clipboard), etc. by clicking the buttons.

Figure 12:
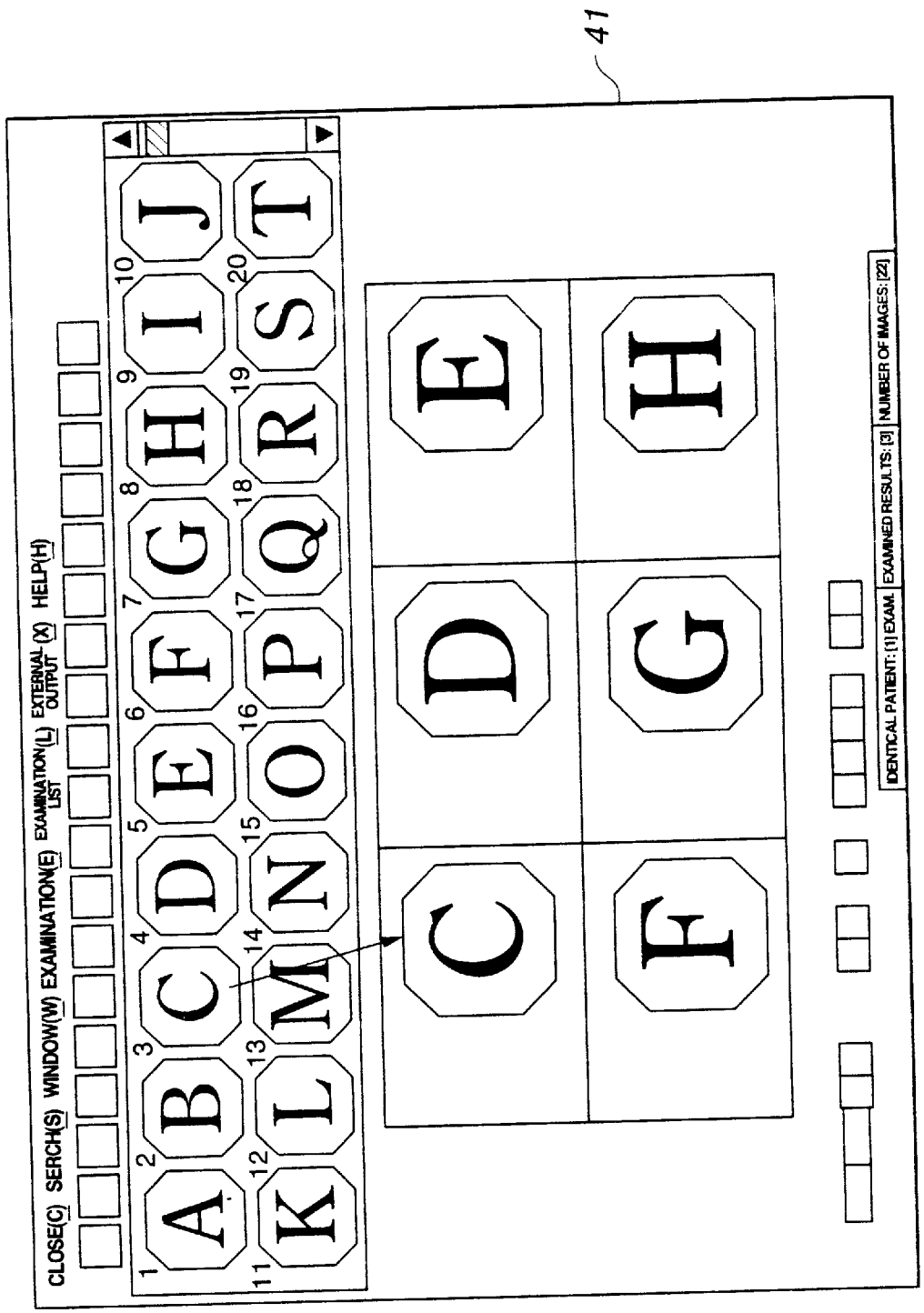
FIG. 12 is an explanatory diagram showing another example of the image display on the image reproduction screen.

In addition, in the case of enlarging and displaying a plurality of index images in the state of FIG. 10, the display layout of the image reproduction screen 31 is altered, as shown in FIG. 12, into an image display screen 41 in a changed-over mode for displaying only the images.

In the image file apparatus 1, the layout of the screen on the monitor unit 5 can be altered into those of various screens meeting the purposes of use, by selecting the menu items prepared in the menu bar 22/the tool bar 23.

By way of example, a desired group of images can be searched for on the basis of a keyword or the like, and the examination list display area 32 is dispensed with thenceforth on condition that a further search such as refined search does not arise. In addition, the remark display area 34 is unnecessary when the image reproduction screen 31 is intended to search for and display the images and is not especially intended to input the remark data.

In such a case, when the full screen is used for the image display, a larger number of images can be simultaneously displayed, and the screen can be used more effectively.

The image display screen 41 has such a layout in which the index images are displayed at the upper part of the screen, and the original images or enlarged images can be displayed at the lower part of the screen. When one of the index images in the upper part of the screen is selected, a predetermined number of images which consist of the selected image and succeeding images are displayed (FIG. 12 exemplifies a 6-image display mode, in which six images with the selected image taken as a reference are automatically selected and displayed).

With the prior-art apparatus, in displaying a plurality of enlarged images in a line (or in lines), all index images to-be-displayed need to be designated one by one, and, therefore, the operation is troublesome. In contrast, according to this embodiment, the plurality of images can be automatically displayed merely by designating one index image, and hence, the troublesome operation is eliminated (in FIG. 12, when the third index image C is designated, the six enlarged images of the successive images which consist of the designated image C and the fourth index image D through the eighth index image H are displayed).

In the application of an image file apparatus for medical service, particularly in the field of an endoscope, images that need to be simultaneously arrayed and displayed are often ones which lie at positions near in a time series. In the field of the endoscope, for example, images are picked up in succession while the endoscope is being inserted into the body. The images which need to be simultaneously arrayed for comparison reference, etc. are ones which lie at positions near in a time series; that is, ones that have been picked up at parts of the same position or near positions. It is rare to compare images that have been picked up at positions being distant in a time series, that is, at remote parts.

Therefore, such a method becomes especially effective, and the operation of the apparatus is freed from troublesomeness and wastefulness. In addition, in the case where the plurality of images are automatically selected and displayed in this manner, any unnecessary image or any image picked up unsuccessfully is displayed. Therefore, the designation of the image to be skipped in the image display, etc. may as well be permitted in order to avoid the display of the undesired image.

Figure 13:
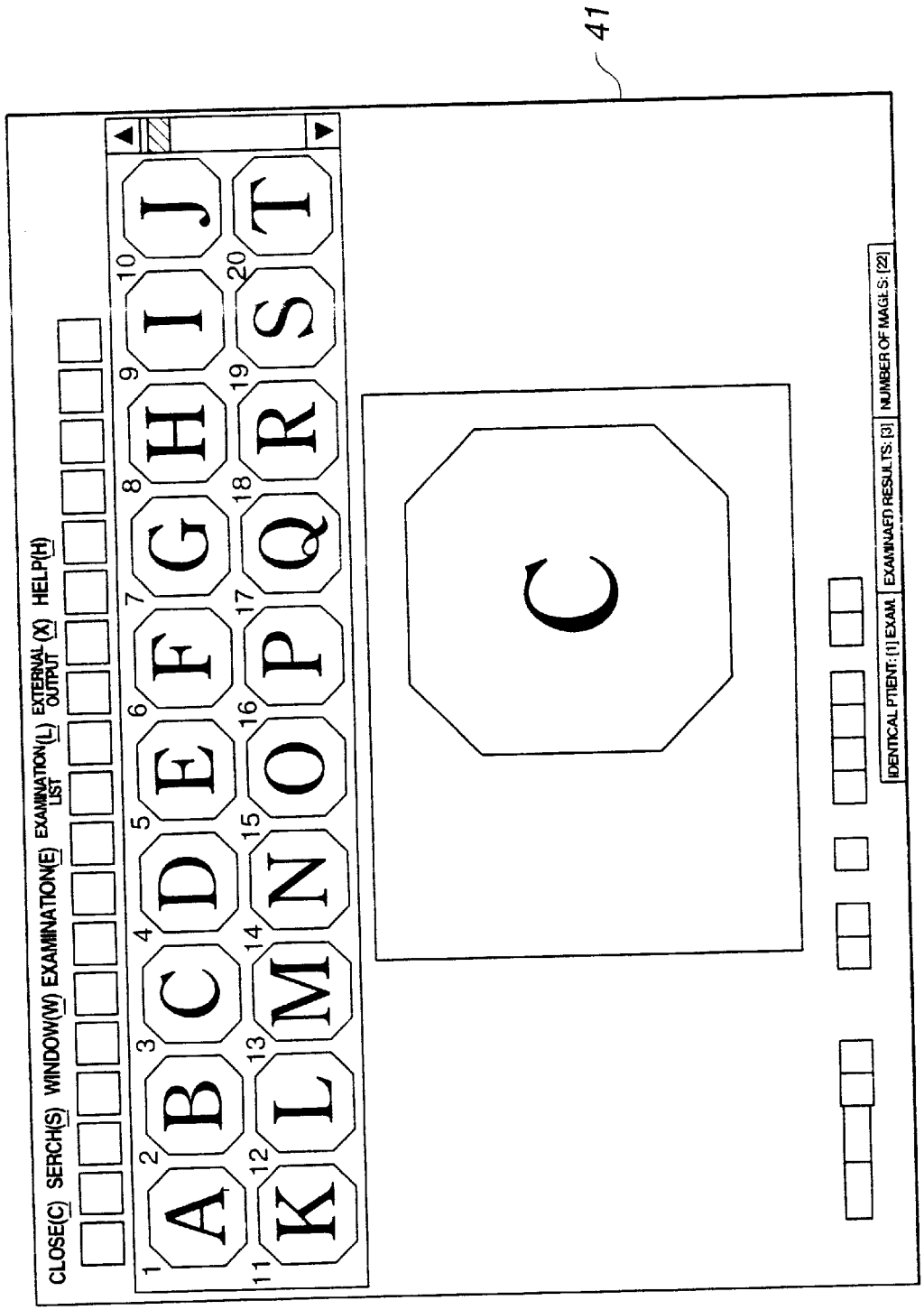
FIG. 13 is an explanatory diagram showing still another example of the image display on the image reproduction screen.
Figure 14:
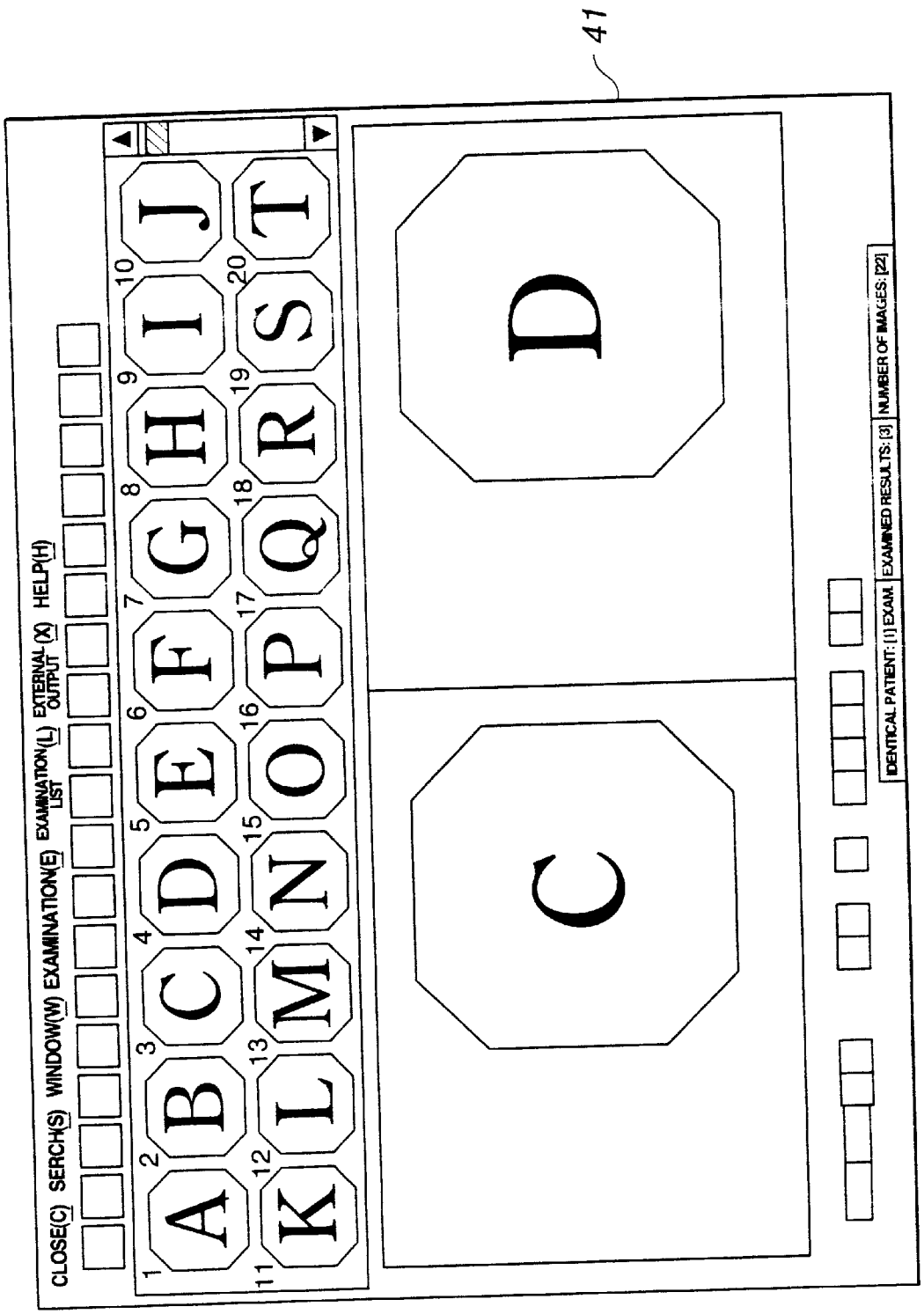
FIG. 14 is an explanatory diagram showing yet another example of the image display on the image reproduction screen.
Figure 15:
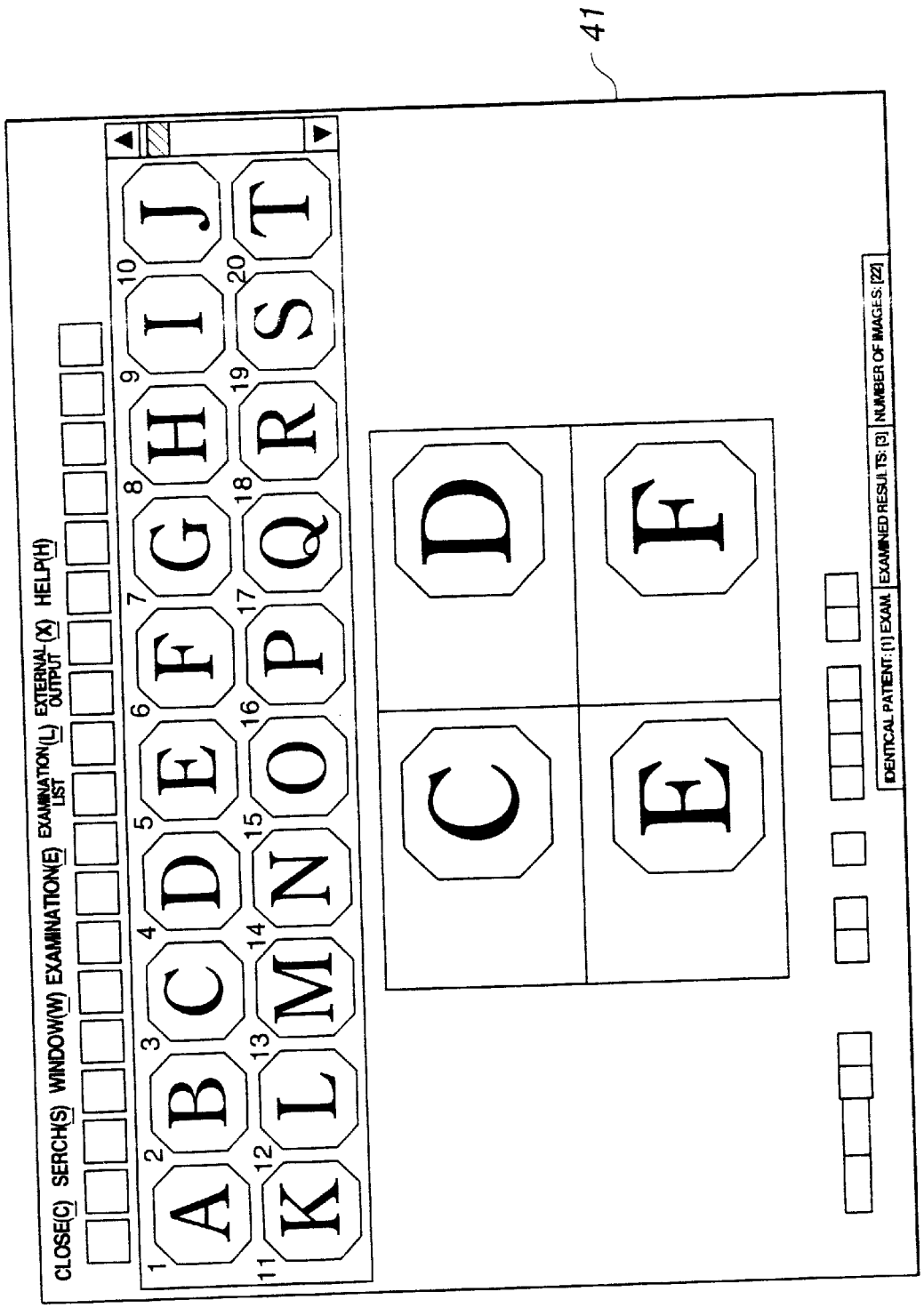
FIG. 15 is an explanatory diagram showing a further example of the image display on the image reproduction screen.

Apart from the 6-image display mode shown in FIG. 12, it is possible to realize a screen layout such as a 1-image mode shown in FIG. 13, 2-image mode shown in FIG. 14, or 4-image mode shown in FIG. 15. As seen from FIGS. 12 through 15, the size of each image to-be-displayed is automatically altered depending upon the number of images to-be-displayed, and the image/images is/are displayed so as not overlap the index images. In this manner, the size is altered in accordance with the number of images to-be-displayed, whereby the screen can be used without being wasted, and the image can be displayed with a larger size.

In the examples of FIGS. 12 through 15, the index images are displayable equally in the number of 20 at one time. The reason for this is that the endoscopic images are often picked up in 20-image units (20 images can be picked up on one roll of silver salt film for an endoscope), so the display of the 20 images as reference is effective.

Figure 16:
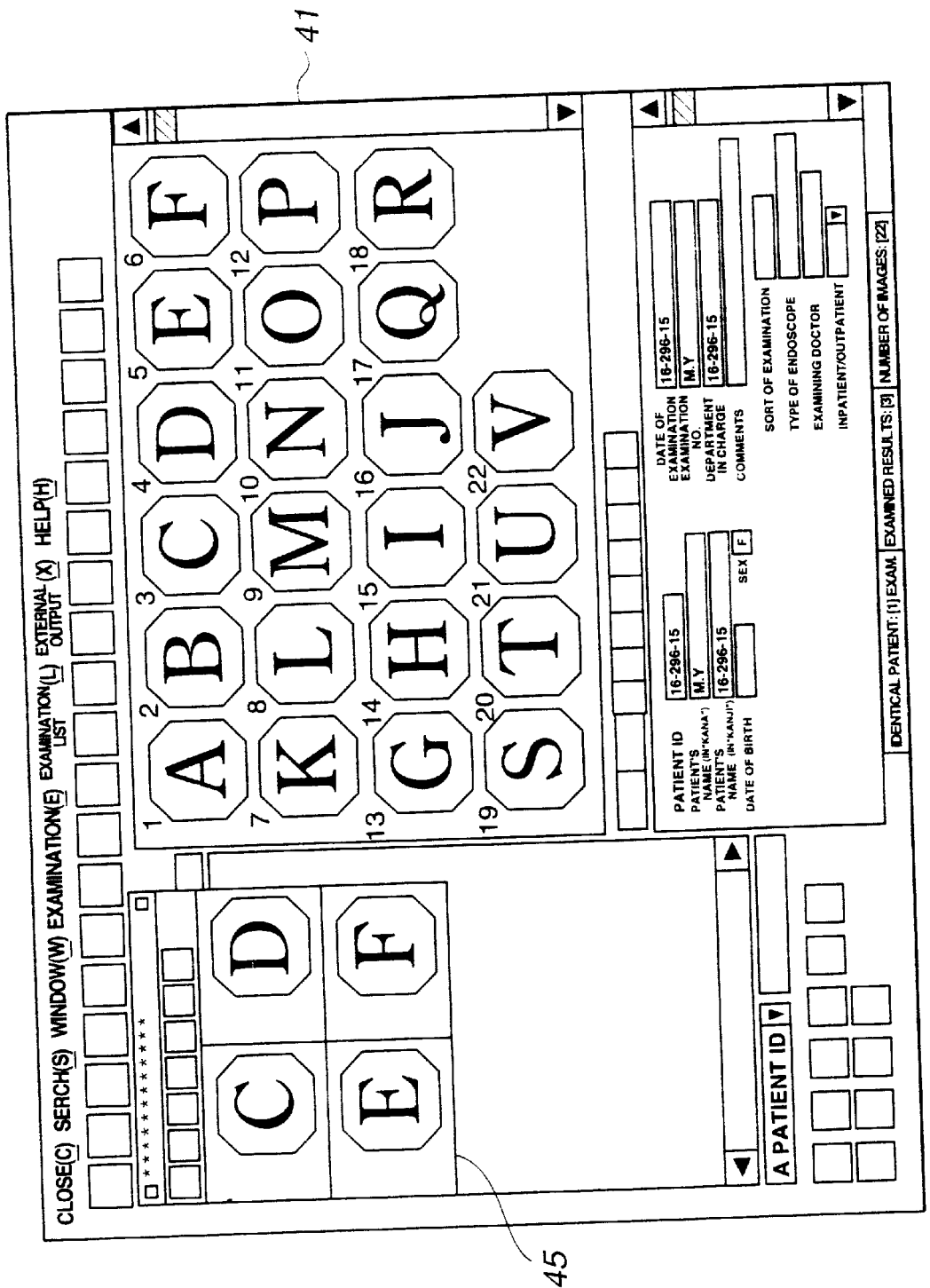
FIG. 16 is an explanatory diagram showing an example of a print preview display on the image reproduction screen.

Meanwhile, FIG. 16 shows a print preview screen 45 in which a plurality of selected images are arrayed for a print output, in the case where the plurality of images have been selected (by, for example, the same method of selecting a plurality of images as in the display mode) by designating the index image in the image reproduction screen 31 shown in FIG. 10. It is the print preview screen 45 that is displayed at the left upper part of the image display screen 41.

Concretely, the print preview screen 45 can be displayed in such a way that the index images in the right upper part of the screen 31 are selected one by one or in the number of four at one time, and that they are dragged and dropped onto a print function icon lying at the left lower part of the screen 31.

Subsequently, a button over the print preview screen 45 is pressed, whereby the displayed contents for print preview can be outputted for printing. Besides, the omission of the print preview can also be set, and the dragged and dropped images may as well be immediately printed. Further, the number of divisions for the printing is not restricted to the 4 divisions, but any of 6, 9 or 12. Twenty divisions can be selected by way of example. The number of divisions can be designated by presetting it or by pressing a button over the print preview screen 45 or one of pop-up icons.

Figure 17:
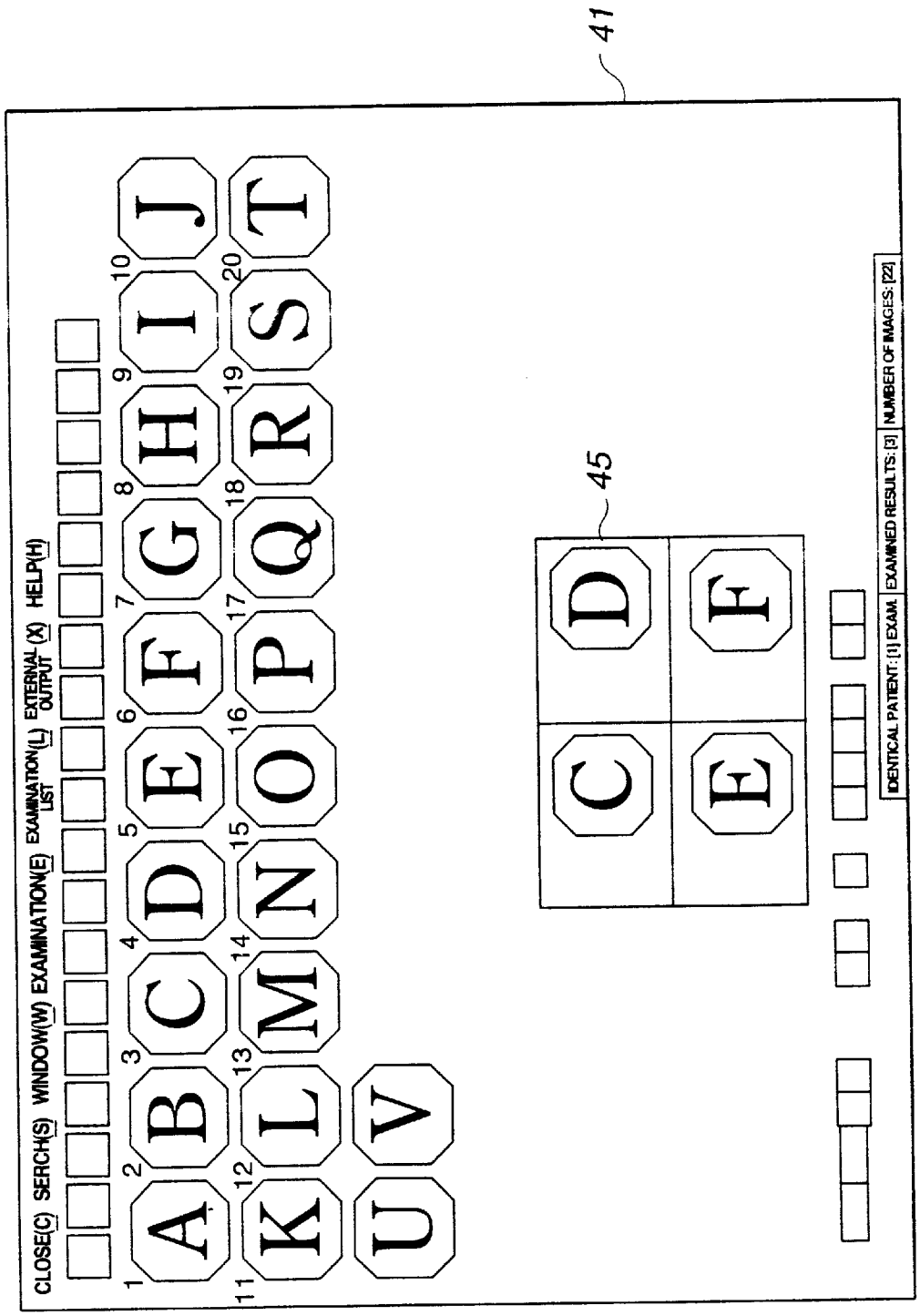
FIG. 17 is an explanatory diagram showing another example of the print preview display on the image reproduction screen.

Also, FIG. 17 shows a print preview screen 45 in which a plurality of selected images are arrayed for a print output, in the case where the plurality of images have been selected (by, for example, the same method of selecting a plurality of images as in the display mode) by designating the index image in the image display screen 41 shown in FIG. 12. The print preview screen 45 corresponds to that displayed in the left upper part in FIG. 16.

Figure 18:
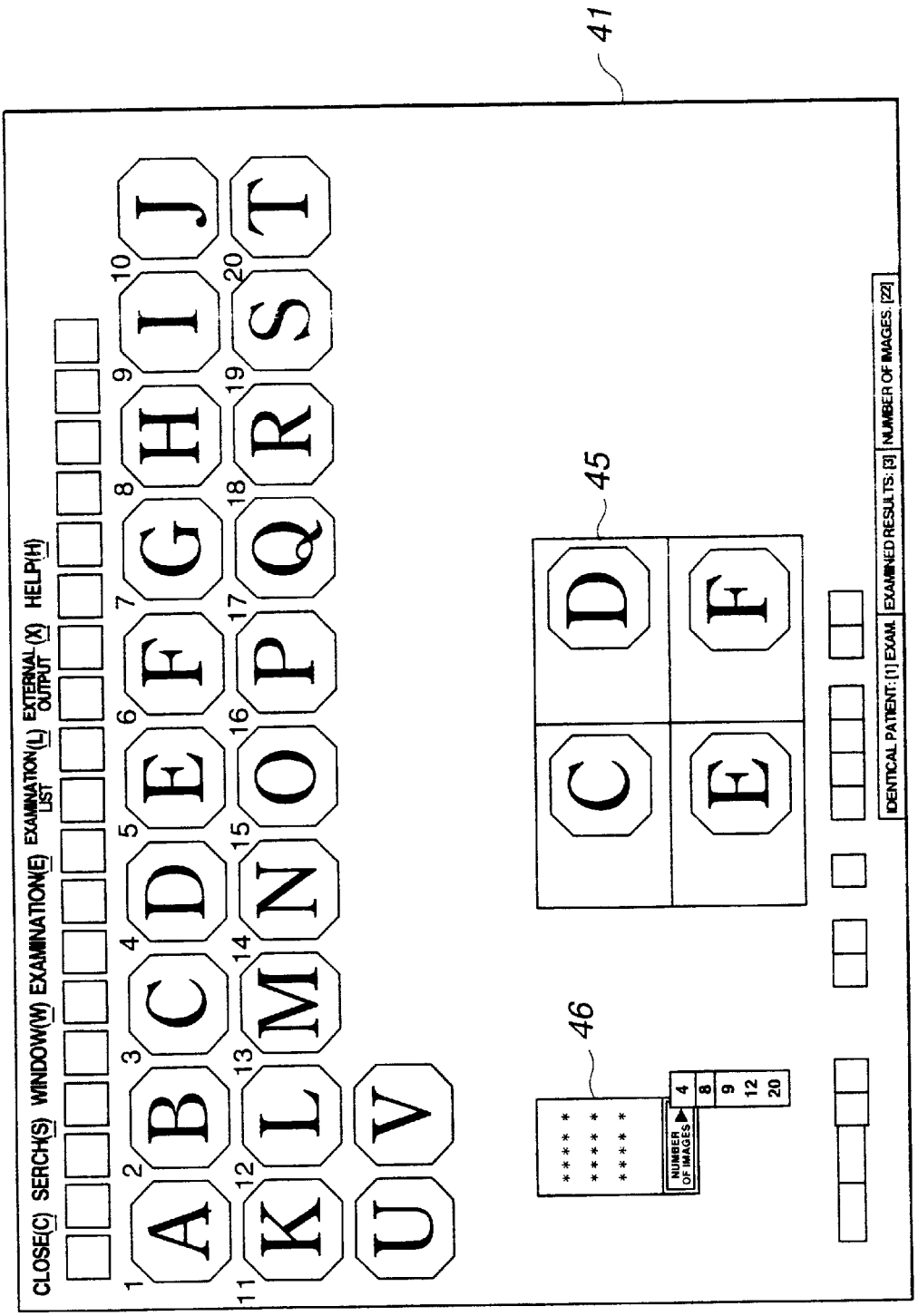
FIG. 18 is an explanatory diagram showing still another example of the print preview display on the image reproduction screen.
Figure 19:
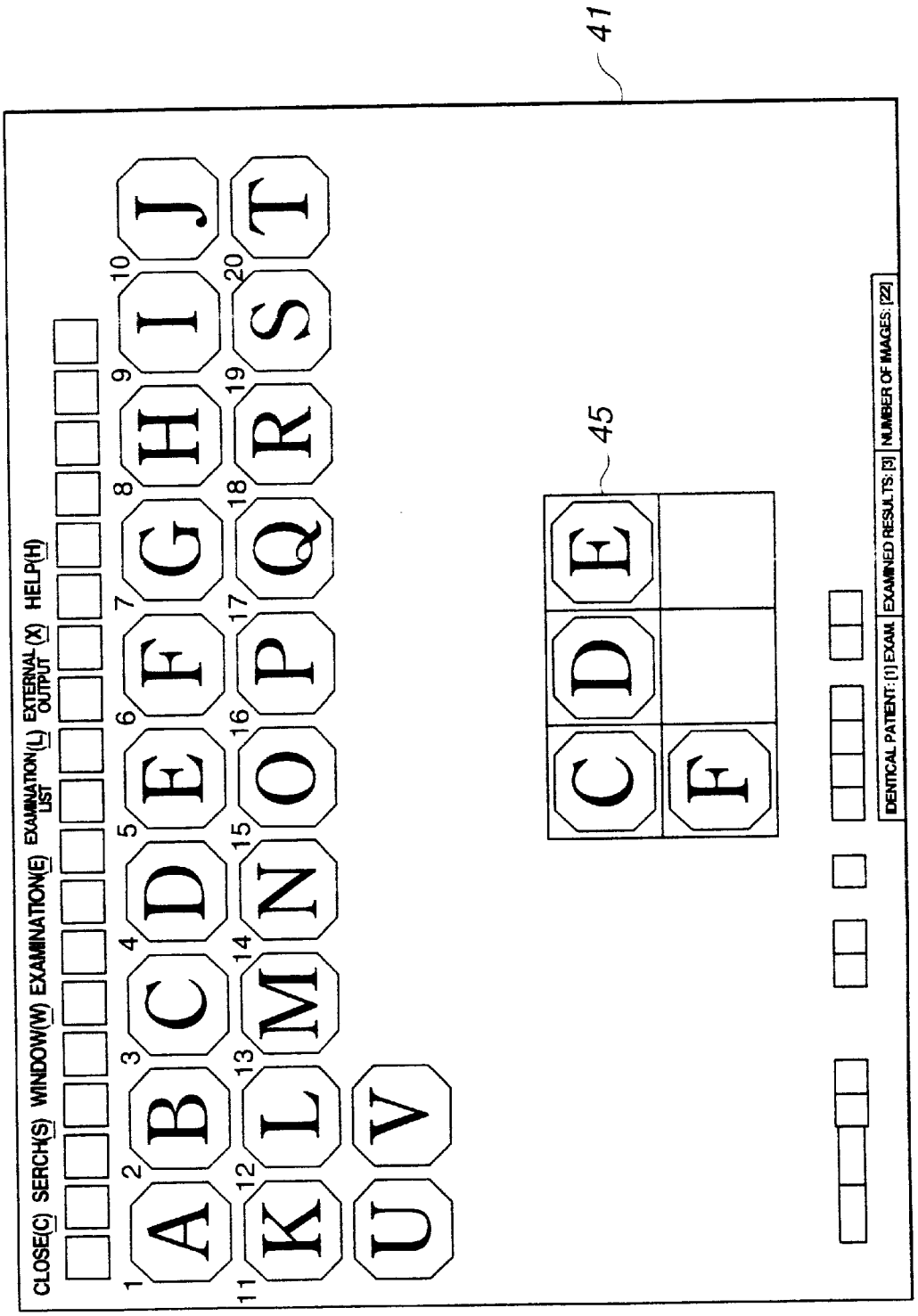
FIG. 19 is an explanatory diagram showing yet another example of the print preview display on the image reproduction screen.

Moreover, with this screen 41, as shown in FIG. 18, a pop-up menu 46 can be displayed so as to select the number of divisions as, for example, 6, by using the mouse 4 in the illustrated state of the print preview screen 45. Then, a display as shown in FIG. 19 is presented.

In the prior art, in selecting images to-be-printed and then printing them, it is required for confirming a print state, not only to perform the operation of selecting each image, but also to give the apparatus the instruction of presenting a print preview display. This poses the problem of troublesome handling. In contrast, according to this embodiment, the print preview screen 45 is automatically displayed in accordance with the operation of selecting the image, and hence, the above problem can be solved.

Further, the display positions of the images can be altered on the print preview screen 45. That is, the image to-be-moved is dragged and dropped onto a desired display position, whereby the display positions are alterable. Therefore, the troublesome operation of re-selecting images is eliminated.

In addition, in the prior art, in displaying a print preview screen, the size thereof is not taken into account, and the print preview screen is displayed overlapping index images, resulting in the problem that the next operation of selecting an image is hampered. In contrast, according to this embodiment, the print preview screen 45 is displayed at the position not overlapping the index images, and hence, the above problem can be solved.

Also, to be previewed and ensured, images are not the detailed contents of the images, but are layout factors such as the positional relations of the images and the number of divisions. In this embodiment, therefore, the size of the image in the print preview screen 45 is set equal to or smaller than that of the index image. An enlarged display, etc. is not required for ensuring the positional relations of the images and the divisional arrangement thereof. Owing to such a limited size, the display area of the screen 45 can be saved, and the part thereof overlapping any other area can be minimized.

Figure 20:
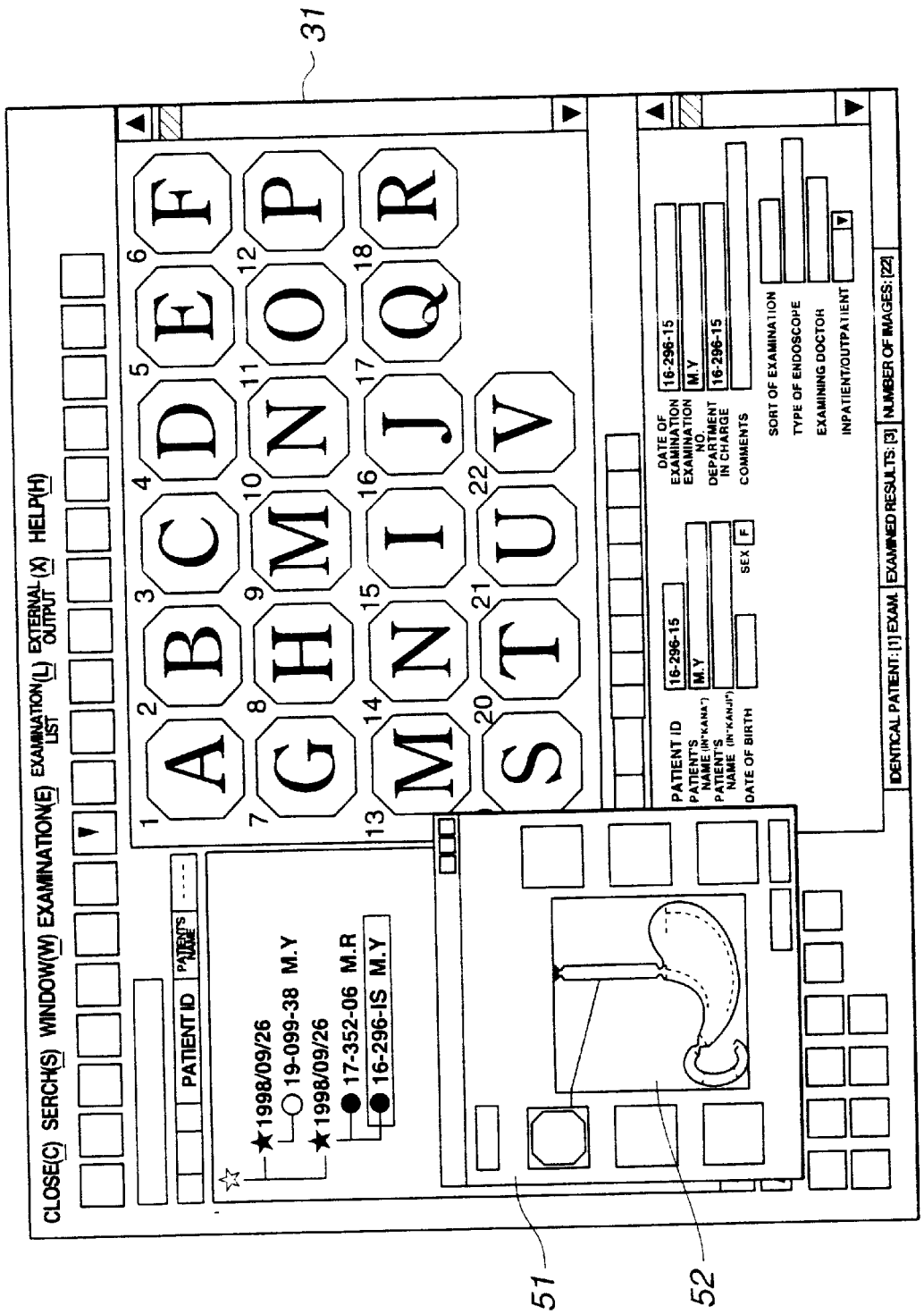
FIG. 20 is an explanatory diagram showing an example of a schema display on the image reproduction screen.

In addition, according to this embodiment, a specified image can be registered in association with remark data. FIG. 20 shows a screen for explaining a registering method therefor. As shown in FIG. 20, an index image selected on the image reproduction screen 31 is dragged and dropped into a window 51 for displaying a diagram which is called a "schema display" and which schematically depicts a viscus, whereby the selected index image is pasted to the schema display window 51. Thus, the selected image can be registered.

In addition, in pasting the selected index image to the schema display window 51, a position on the schema display 52 in the schema display window 51 is designated, whereby the picked-up region of the image can be indicated. The schema display window 51 can be displayed by performing a predetermined operation such as pressing a button in the remark display area 34 or right-clicking the mouse 4 in the remark display area 34.

Figure 21:
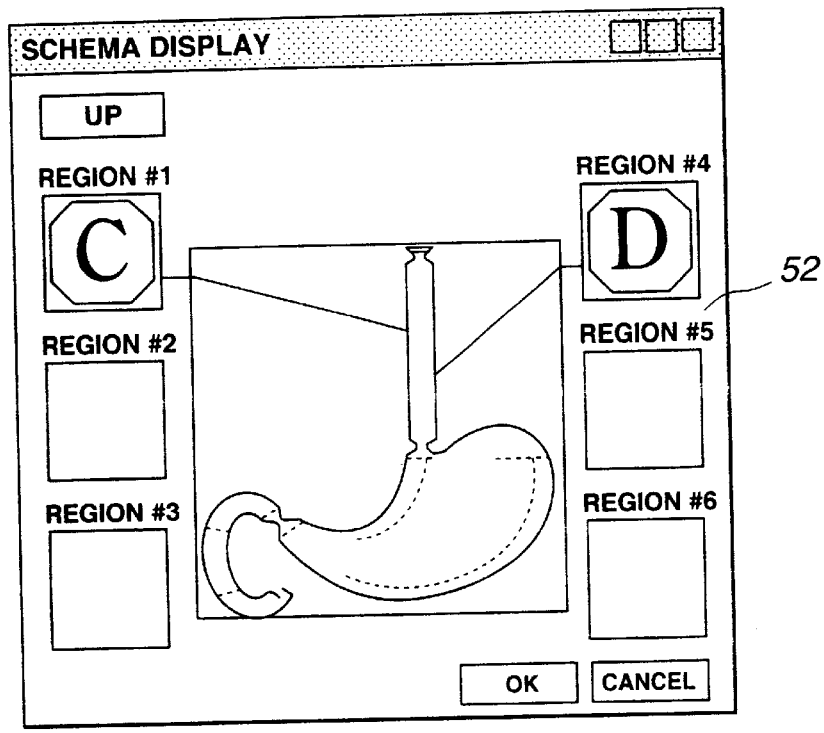
FIG. 21 is an explanatory diagram showing an example of the schema display.
Figure 22:
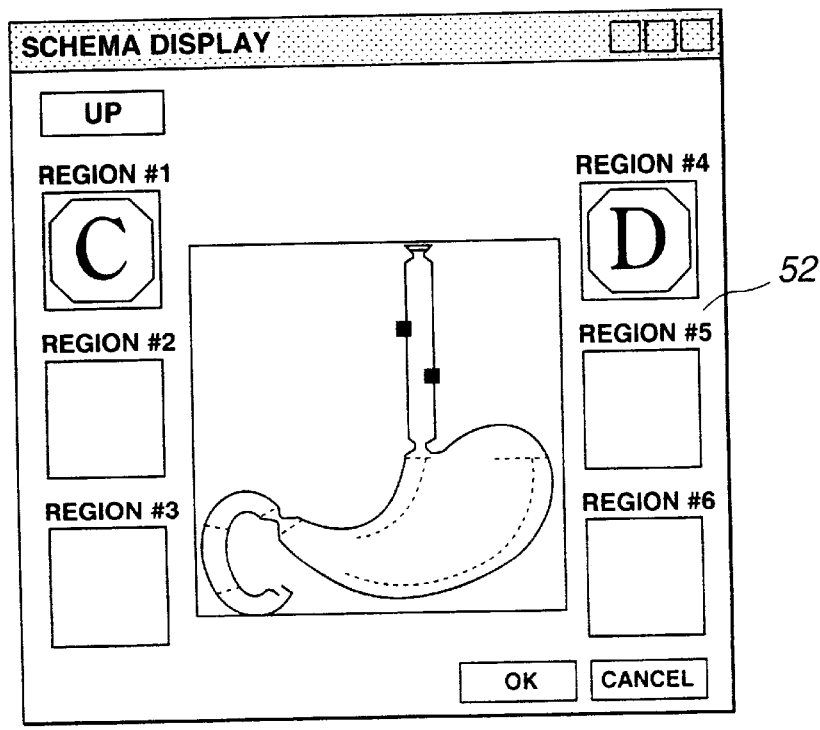
FIG. 22 is an explanatory diagram showing another example of the schema display.

As shown in FIGS. 21 and 22, the region to which the picked-up image corresponds is displayed by designating the position of the picked-up region. FIG. 21 shows an example in which the position is indicated by a line, while FIG. 22 shows an example in which the position is indicated by marking.

Figure 23:
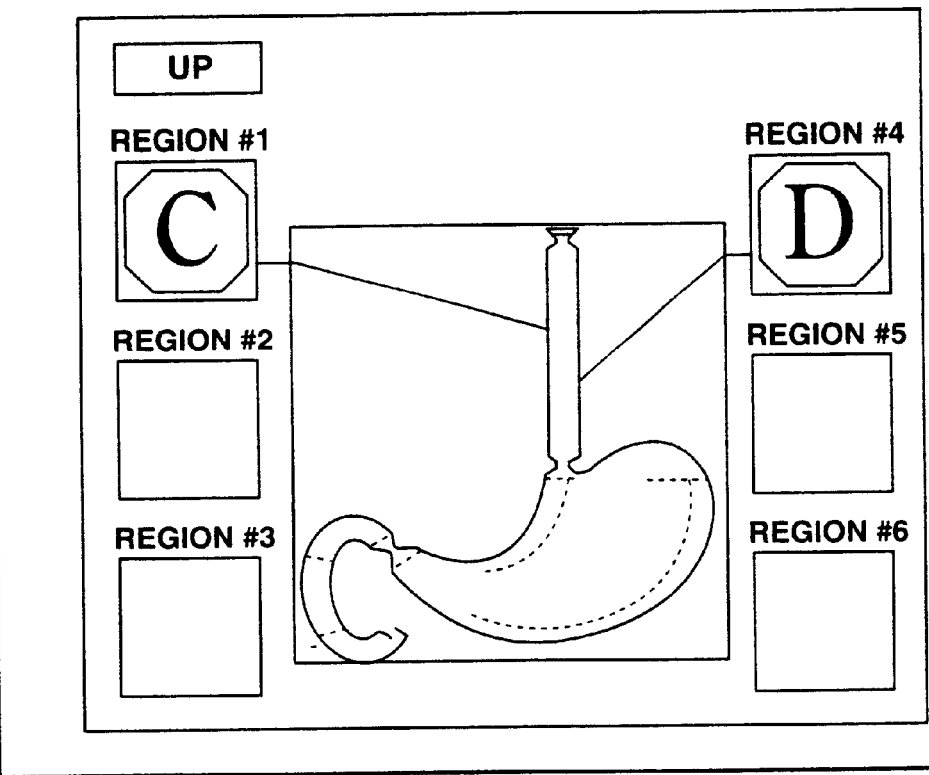
FIG. 23 is an explanatory diagram showing a print example of the schema display.

FIG. 23 shows an output result obtained in such a way that the remark data registered by inputting it from the remark display area 34 in the image reproduction screen 31, and the image registered using the schema display window 51, are outputted for printing. In this embodiment, a remark window displayed in the remark display area 34 is dragged and dropped onto the print function icon of the object copy area 35, whereby the remark data and the schema display 52 registered in association therewith can be outputted for printing as a remark document 55.

Meanwhile, the image file apparatus 1 is of the stand-alone type. It is so constructed that the database 11 is referred to from the hard disk 2a of the apparatus main body 2, while the image data 12 are referred to from the MO medium 8a inserted in the MO unit 8. Therefore, the database 11 can be always accessed for searches etc., but the image data 12 can be displayed only for images which are recorded in the MO medium 8*a* inserted in the MO unit 8. Accordingly, when an image specified by a search is to be displayed, a specified MO medium 8*a* in which the image has been recorded needs to be inserted into the MO unit 8.

Figure 24:
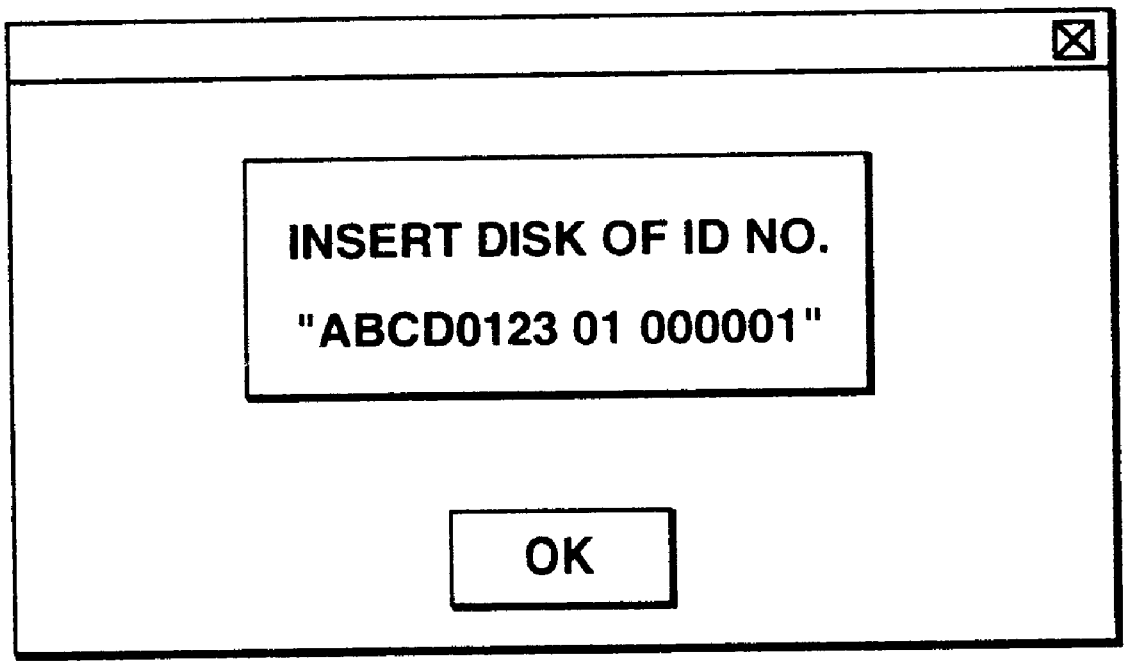
FIG. 24 is an explanatory diagram showing a display example of a screen which requests an operator to insert an MO medium.

In the image file apparatus 1, as described before, the storage medium IDs of MO media and examination data are managed in association within the database 11. When an image is to be displayed, the storage medium ID of the MO medium 8*a* that needs to be inserted is displayed, for which the user is permitted to quickly select the predetermined MO medium 8*a* and then insert it into the MO unit 8. An example of a message display on this occasion is shown in FIG. 24.

Moreover, when the search results of endoscopic examinations are displayed as a list in the examination list display area 32 (refer to FIG. 10), a storage medium ID display 32*a* is conjointly presented so as to grasp in which MO media 8*a* the individual examinations indicated in the list are recorded. Therefore, in the case where the desired image is to be displayed, the user can quickly know the required MO medium 8*a*.

In this regard, the MO medium 8*a* may as well be selected in such a way that the aforementioned storage medium ID display 32*a* which is presented as, for example, "ABCD0123 01 00000" is attached to a message or indicated on the examination list display area 32 as it is. It is apprehended, however, that the No. display that is the mere string of numerals will be illegible or will necessitate labor for discrimination due to the large number of digits. It is therefore recommended to convert the storage medium ID display 32*a* into a number having a smaller number of digits or into an appellation having a significance, and to display the resulting number or appellation. By way of example, in the case where the storage medium ID is "ABCD0123 01 000001", a display "No. 1-1-Facilities OΔ" is considered. On this occasion, displays like the example can be presented in such a way that rules for converting the storage medium IDs are recorded and managed as table data in the hard disk 2*a* of the apparatus main body 2.

Figure 25:
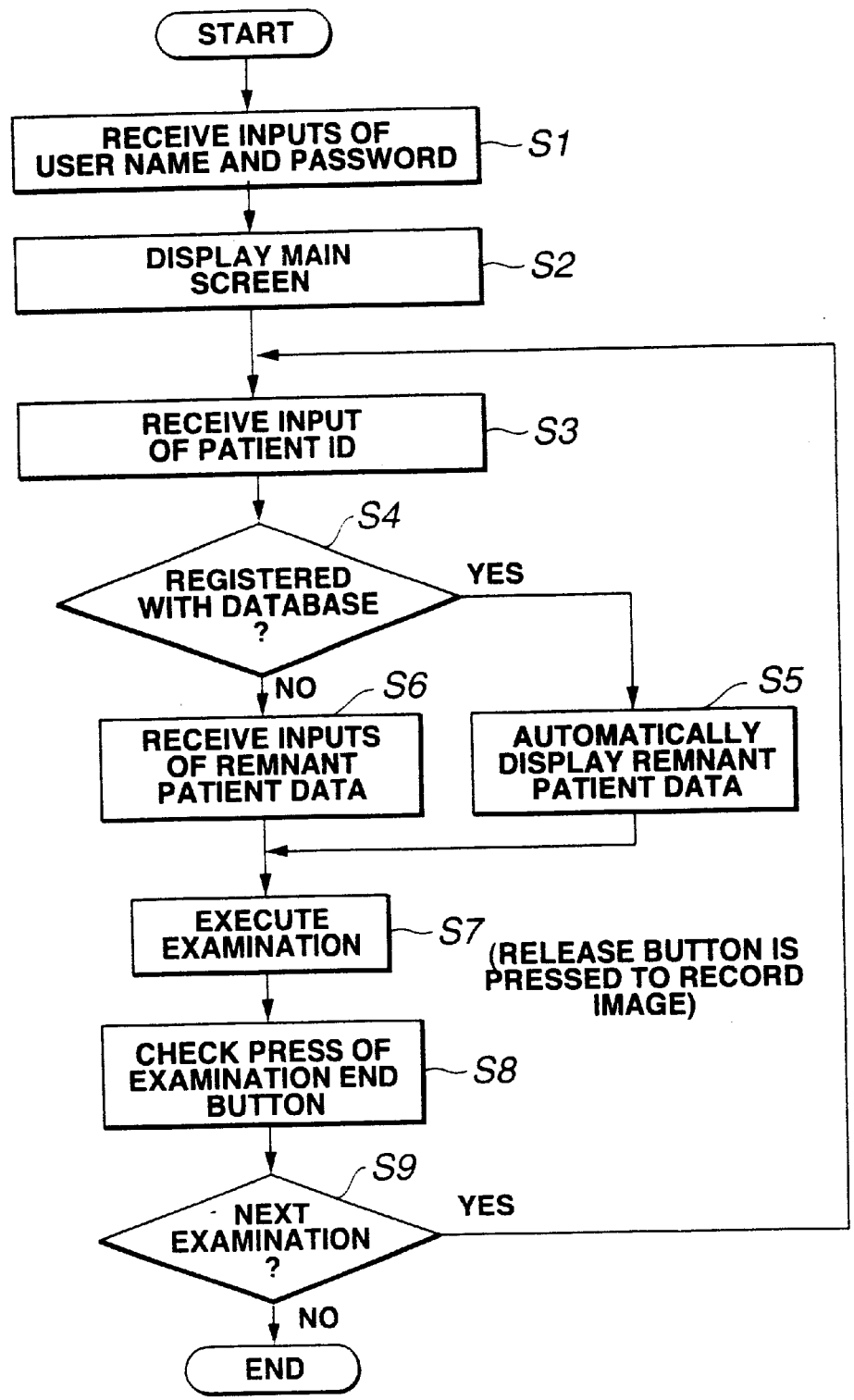
FIG. 25 is a flow chart showing the flow of processing steps in an examination mode.

Now, the flow of processing steps in an examination mode will be described with reference to FIG. 25.

First, a user name and a password are inputted at a step S1, for which the main screen 21 is displayed as indicated at a step S2.

Subsequently, as indicated at a step S3, the patient ID of a patient to-be-examined is inputted to the endoscope unit 6 or the apparatus main body 2. The subsequent step S4 serves to decide whether or not the patient to-be-examined has already been registered with the database 11 because he/she has been examined by way of example. In a case where the pertinent patient has already been registered, other data concerning him/her can be searched for on the basis of his/her patient ID. Therefore, the remnant patient data (such as name, date of birth, and sex) are automatically displayed as indicated at a step S5. On the other hand, in a case where the pertinent patient has not been registered with the database 11 yet and where the patient data are not automatically displayed, the remnant patient data are inputted as indicated at a step S6.

When the patient data have been automatically displayed or have been inputted, the examination is ready, and hence, it is executed as indicated at a step S7. The details of the execution of the examination at the step S7 will be explained later. In a case where, at the end of the execution of the examination, the next examination is further made as indicated at a step S9, the control flow returns to the step S3, and the series of processing steps concerning the examination are repeated.

Figure 26:
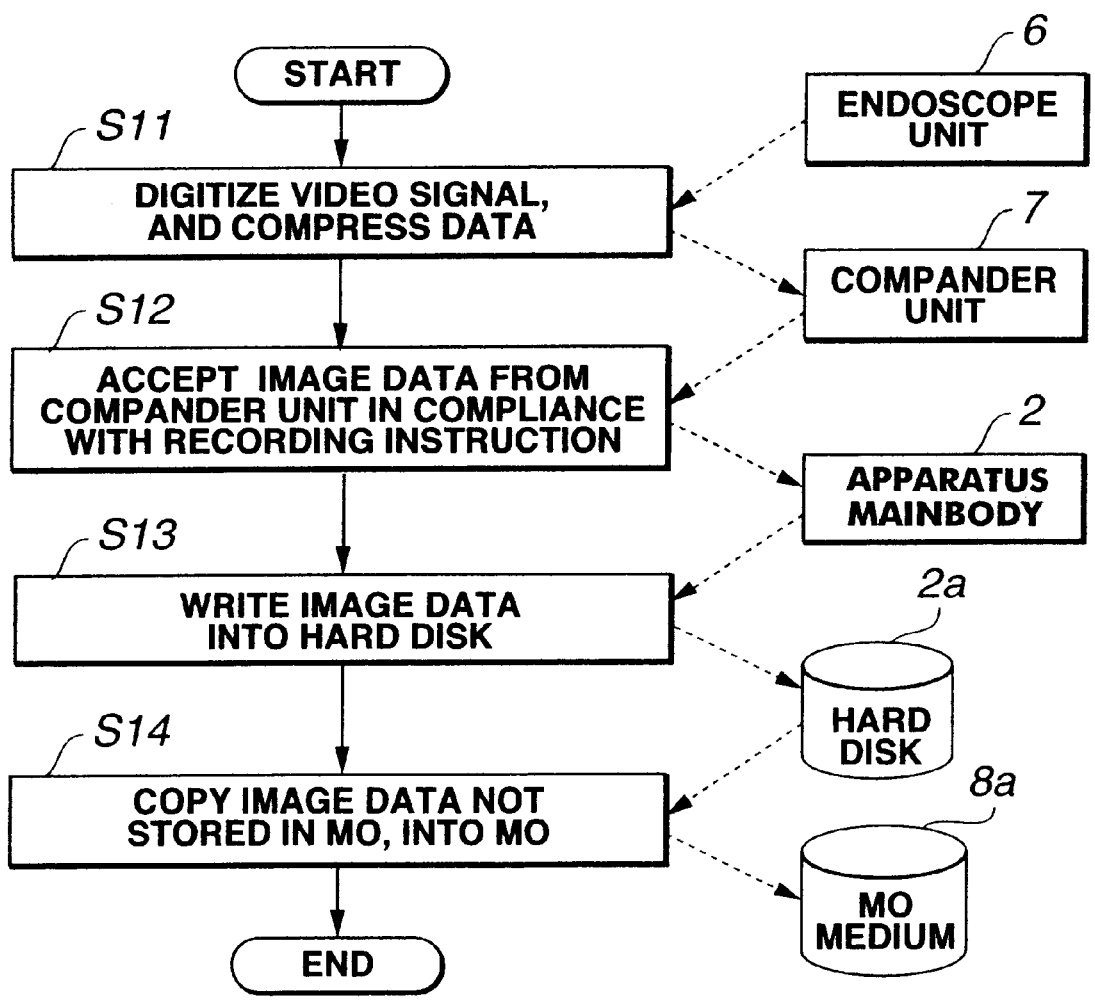
FIG. 26 is a flow chart showing the flow of processing steps in the execution of an examination.

Now, the flow of the execution of the examination at the step S7 will be described with reference to FIG. 26. In the execution of the examination, as indicated at the first step S11, the compander unit 7 complies with a release command from the endoscope unit 6 to convert a video signal including image data from the endoscope unit 6, into a digital signal, and to compress the image data. At the subsequent step S12, the image data compressed at the step S11 are accepted into the apparatus main body 2 in compliance with a recording instruction, and at the subsequent step S13, the image data are written into the hard disk 2*a*. In addition, at the subsequent step S14, the image data are cooled from the hard disk 2*a* into the MO medium 8*a*. After several images have been recorded in this way, an execution end button is manipulated in the endoscope unit 6 or the apparatus main body 2 (at a step S8 in FIG. 25), whereby one time of examination execution is ended.

Now, the operation of securing the capacity of the used hard disk 2*a* will be described. As explained above, the released image is recorded in the hard disk 2*a* of the apparatus main body 2 and is subsequently copied into the MO medium 8*a*. Herein, unlike the exchangeable MO medium 8*a*, the recording capacity of the hard disk 2*a* is finite, so that the recorded data need to be erased. In the apparatus 1, therefore, the data having been copied into the MO medium 8*a* are erased successively from older ones. On this occasion, the status of whether or not the image data have been copied into the MO medium 8*a* can be known by checking the MO copy flag 15*a* (refer to FIG. 5) of the image management table 15. By way of example, when the image file apparatus 1 has been started or ended or when an erasing instruction has been manually given by the user, the data having been copied into the MO medium 8*a* are erased from the hard disk 2*a*, for which the capacity of the hard disk 2*a* can be secured. In addition, in the erasing operation, all the data having been copied need not be erased from the hard disk 2*a*, but the data corresponding to a capacity to be secured should preferably be erased. Thus, regarding examinations recently made, the image data remain in the hard disk 2*a*, and the image can be restored and displayed from the hard disk 2*a* without exchanging the MO media 8*a*.

Figure 27:
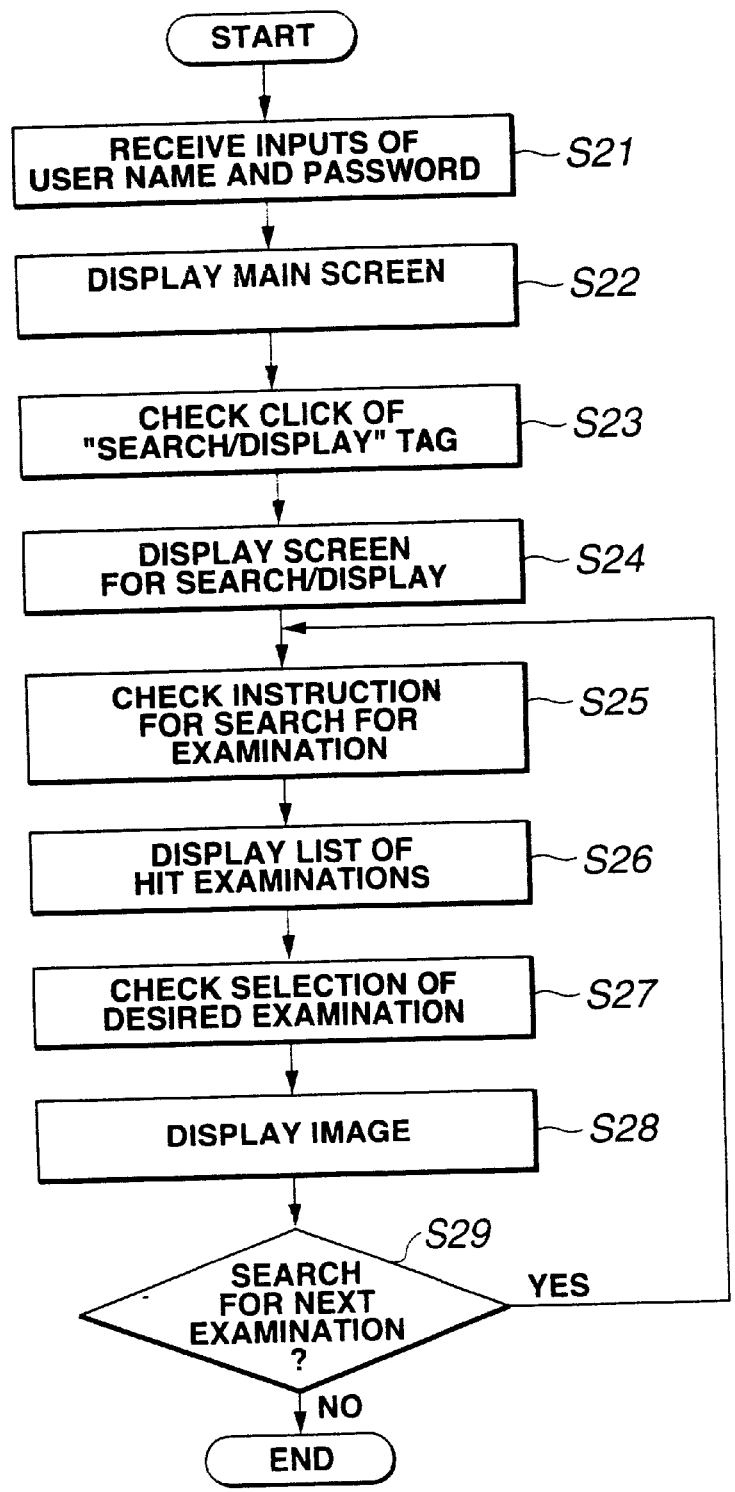
FIG. 27 is a flow chart showing the flow of processing steps for searching and displaying of images.

Now, the flow of processing steps for searching for and displaying an image will be described with reference to FIG. 27. First, when a user name and a password are inputted at a step S21, the main screen 21 is displayed as indicated at a step S22. By the way, when the main screen 21 has already been displayed on this occasion because of, for example, the completion of an examination, the user name and the password need not be inputted at the step S21. Subsequently, as indicated at a step S23, the search/display tag 27 is clicked on the main screen 21, for which the screen for search/display, namely, the image reproduction screen 31 is displayed as indicated at a step S24. Here, when a search for a desired examination is instructed by inputting patient data and examination data as indicated at a step S25, the database 11 managed in the hard disk 2*a* is searched, and hit examinations matching with search conditions are displayed as a list as indicated at a step S26. Thereafter, as indicated at a step n 27, the examination whose image is to be displayed is selected from within the displayed examination list. Then, the image recorded in the selected examination is displayed at a step S28 which will be detailed below. At the subsequent step 329, another examination is further searched for so as to display the image thereof, the control flow is returned to the step S25, from which the series of operations concerning the image display are repeated.

Figure 28:
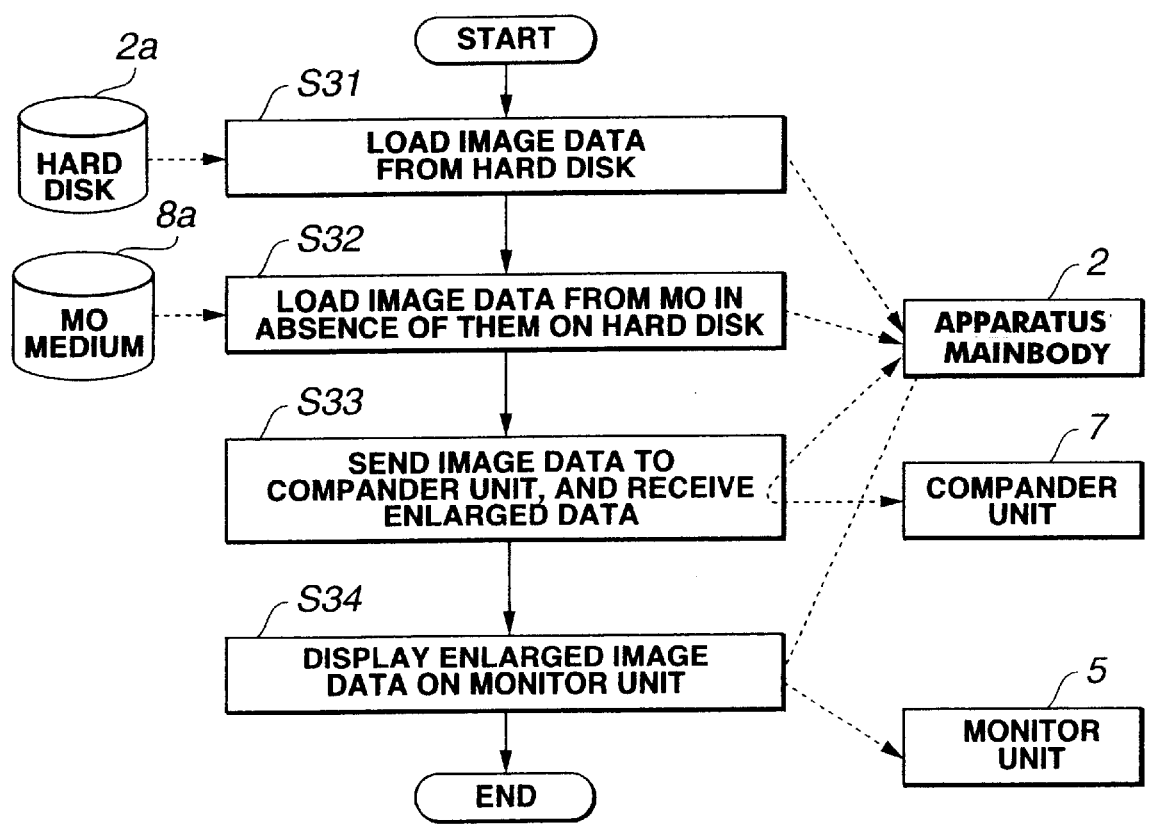
FIG. 28 is a flow chart showing the flow of processing steps for displaying an image.

Now, the processing flow of the image display at the step S28 will be described with reference to FIG. 28. First, at a step S31, image data are loaded from the hard disk 2a by the apparatus main body 2. However, when data have been erased from the hard disk 2a, so the desired data do not exist in the hard disk 2a, data are loaded from the MO medium 8a by the apparatus main body 2 as indicated at a step S32. Further, when the desired image data are not recorded in the MO medium 8a inserted in the MO unit 8, the storage medium ID of the required MO medium 8a is displayed, and the user is requested to exchange the MO media 8a, as shown in FIG. 24. As indicated at a step S33, the image data thus loaded are sent to the compander unit 7 so as to be expanded, and the expanded data are received by the apparatus main body 2 again. Thereafter, the expanded image data are displayed on the monitor unit 5 as indicated at a step S34.

There will now be described a function which shall be conveniently called "import function", and by which data are shared in an image file system utilizing a plurality of image file apparatus 1.

In facilities of medium scale where a network type system of large scale is unnecessary, but where a single image file apparatus of stand-alone type is insufficient, an operational control employing a plurality of stand-alone type image file apparatus 1 is suggested. Here an environment will be assumed where two image file apparatus 1, namely, an image file apparatus 1a and an image file apparatus 1b are existent.

Usually, in the apparatus of the stand-alone type, a database is not shared as in the network type system. Therefore, certain data can be utilized by only one apparatus which manages the data.

Figure 29:
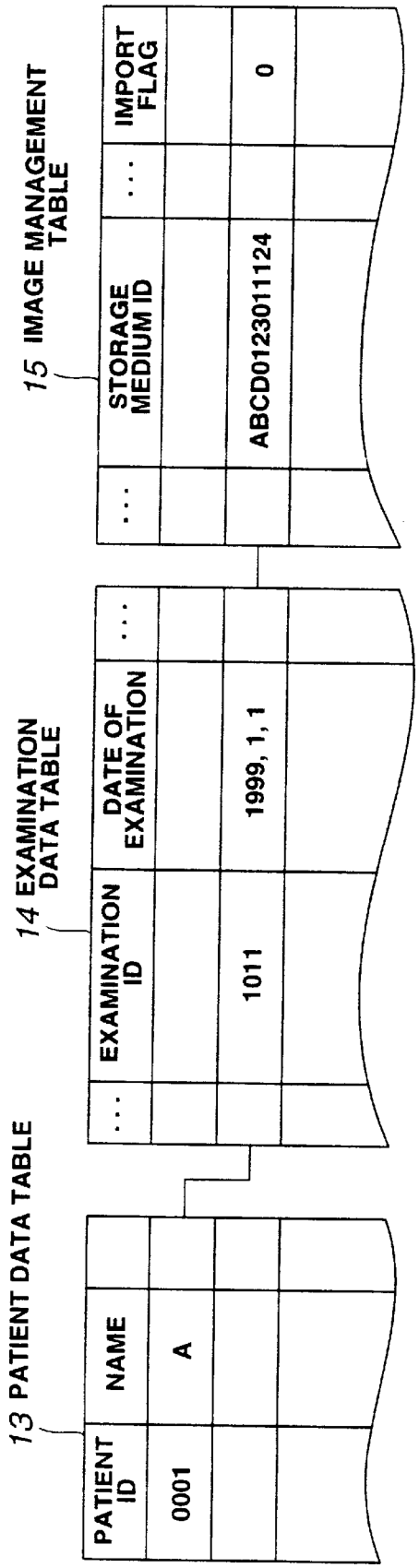
FIG. 29 is an explanatory diagram showing the relationships among a patient data table, an examination data table and an image management table as are referred to in the explanation of an import function.

By way of example, in a case where a patient A whose patient ID is "0001" has been examined on the side of the image file apparatus 1a, the patient data table 13, the examination data table 14 and the image management table 15 are associatedly stored in the database 11 of the image file apparatus 1a as shown in FIG. 29. As stated before, the patient data table 13 contains the patient data such as "patient ID" and "name", the examination data table 14 contains the examination data such as "examination ID" and "date of examination", and the image management table 15 contains the image management data such as the "storage medium ID" of the MO medium 8a in which an image is stored. In such a state where the examination has been made, and where the data items are managed in the database 11, the MO medium 8a in which the image is recorded, namely, the MO medium 8a which is to be inserted into the MO unit 8, can be specified by making a search on the basis of the name of the patient, the date of the examination, or the like. The image can then be reproduced and displayed after the insertion of the MO medium 8a. Simultaneously therewith, the inputted data items managed in the database 11 can be displayed and effectively utilized for aiding in a diagnoses, explaining the result of the examination to the patient, and so forth. In addition, when the patient has been examined once and the patient data are registered with the database 11 in this manner, only the patient ID may be inputted to the apparatus main body 2 in examining the patient again, for which the other data such as "name, date of birth, and sex" can be automatically read out of the database 11 and displayed on the monitor unit 5.

However, the data items are managed in only the database 11 of the image file apparatus 1a, and they are not registered on the side of the other image file apparatus 1b, so that the examination data cannot be displayed on the side of the image file apparatus 1b. In addition, when the reexamination of the patient A is intended on the side of the image file apparatus 1b, the other data cannot be read out and automatically displayed even by inputting the patient ID. Therefore, the image file apparatus 1a and 1b are permitted to share the data by a contrivance stated below.

Figure 30:
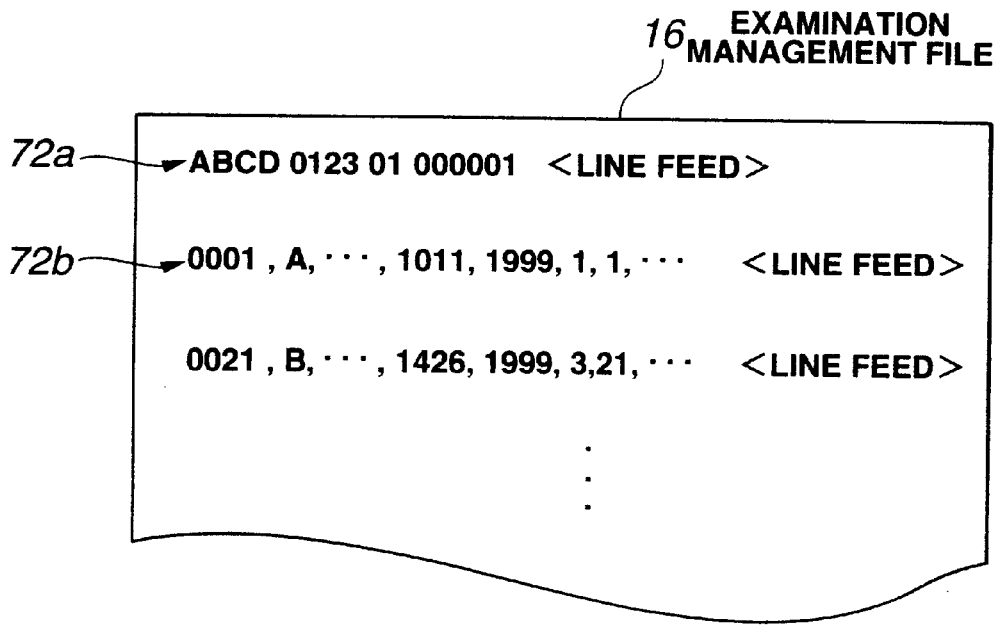
FIG. 30 is an explanatory diagram showing the data layout of an examination management table.

FIG. 30 shows the data contents of the examination management file 16 recorded in the MO medium 8a. The examination management file 16 is one in which the patient data and examination data associated with the image data retained in the MO medium 8a are collectively recorded. This file 16 is created in every MO medium 8a, and is described in, for example, the CSV format (a format where data items are partitioned by "," (comma)).

A record 72a at the first line of the examination management file 16 is the storage medium ID given to the pertinent MO medium 8a. The patient data and the examination data recorded in each examination are retained in each of the records at the second line, et seq. That is, line feed is done every examination. By way of example, the examination of the patient "A" indicated in FIG. 29 is recorded as a record 72b in the examination management file 16 shown in FIG. 30.

In this manner, not only the image data released in the examination, but also data concerning the examination of the recorded image data are stored as the examination management file 16 in the MO medium 8a. The image file apparatus 11b can obtain the data registered with the image file apparatus 1a, by loading the examination management file 16. Loading the examination management file 16 shall be called "import" for the sake of convenience in this specification.

On this occasion, the data relevant to the examination as loaded by the import function are identified by the fact that an import flag 15b (in FIG. 29) in the image management cable 15 falls into the status of "1" (ON). Since the examination of the patient A has been made on the side of the image file apparatus 1a, the import flag 15b in the image management table 15 of the image file apparatus 1a is "0" (OFF) in FIG. 29. Assuming that the examination has been made on the side of the image file apparatus 1b, and that the data have been imported to the image file apparatus 1a, the import flag 15b is turned into "1" (ON) so as to identify that the data have been obtained by the import function.

Figure 31:
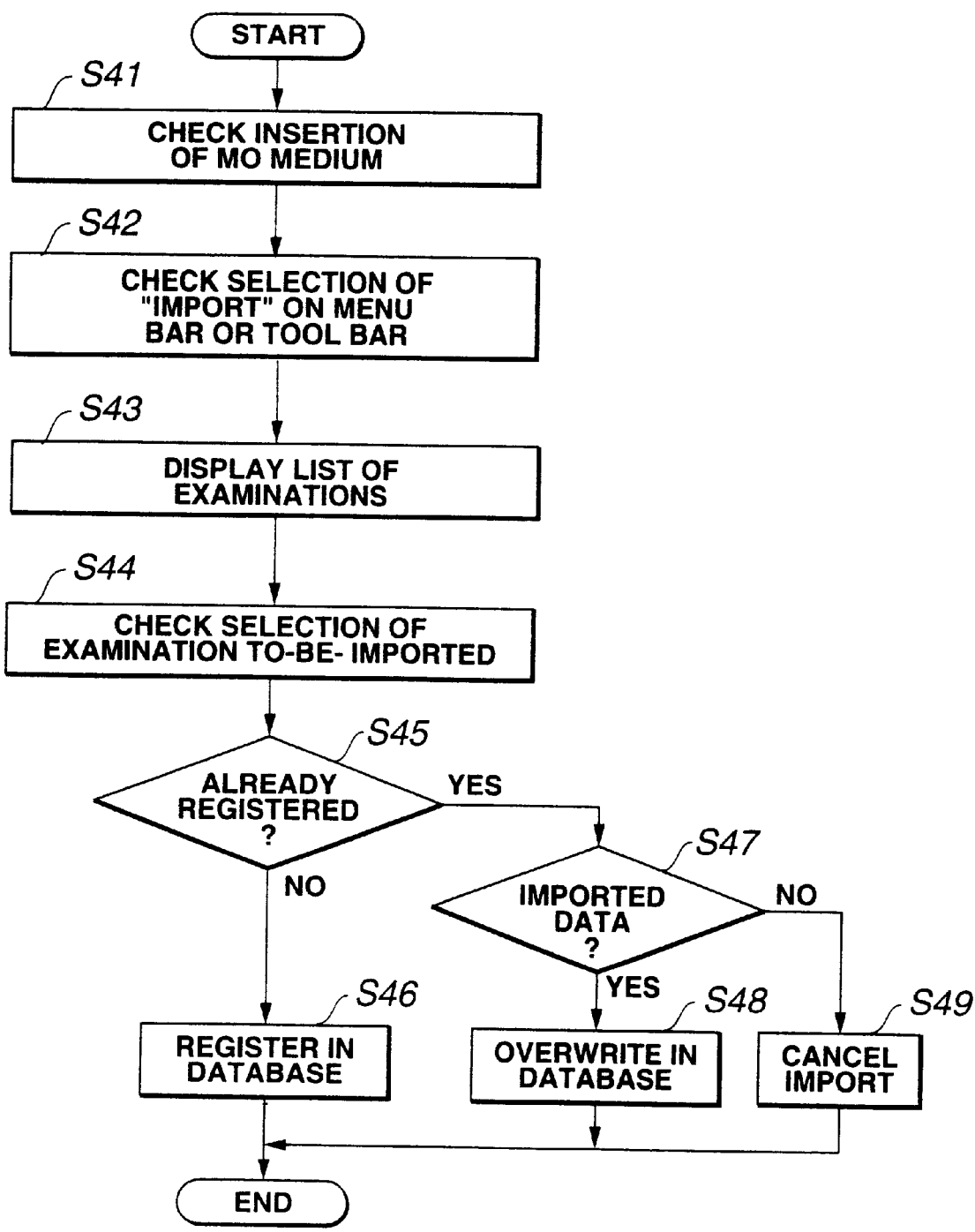
FIG. 31 is a flow chart showing the flow of processing steps in the import function.

The flow of Processing steps for importing data relevant to a desired examination will be described with reference to FIG. 31.

First, at a step S41, the MO medium 8a in which the data of the examination to be imported are recorded is inserted into the image file apparatus 1, which is an importing destination.

Subsequently, at a step S42, the "import" function is selected by manipulating the menu bar 22 or tool bar 23 on the main screen 21.

Figure 32:
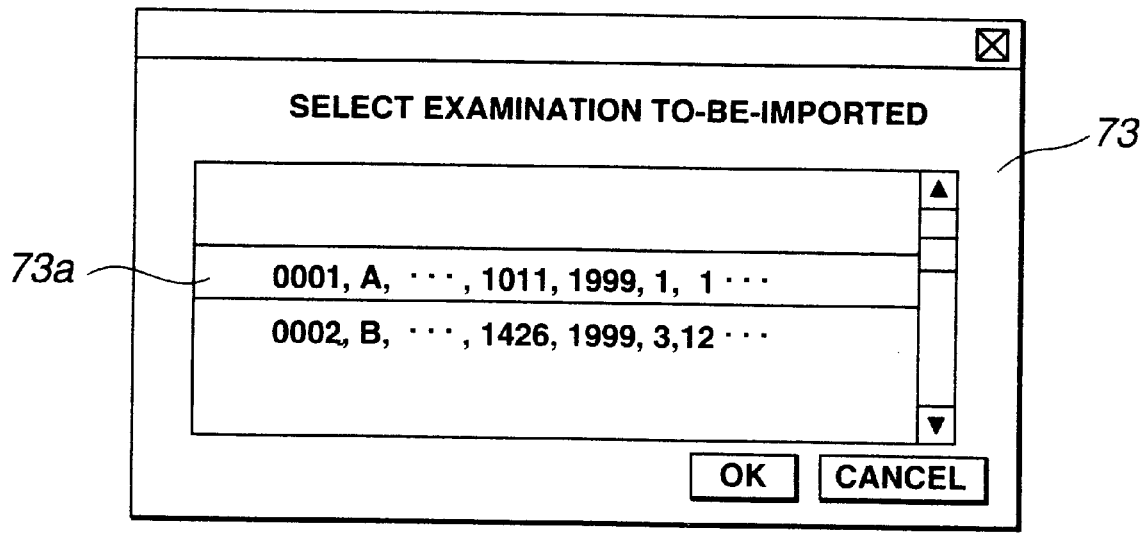
FIG. 32 is an explanatory diagram showing a display example of a selection screen for selecting an examination as is referred to in the explanation of the import function.

Then, the examination management file 16 is read out of the MO medium 8a, and a selection screen 73 shown in FIG. 32, for selecting the examination to-be-imported is displayed as indicated at a step S43. The selection screen 73 displays the list of examination management data which correspond to the contents of the examination management file 16 read out of the MO medium 8a. At the subsequent step S44, the desired examination management data is brought into a reverse display 73a shown in FIG. 32, and a button "OK" is pressed, for which the examination management data is selected. On this occasion, a plurality of items of examination management data can also be selected by bringing them into reverse displays 73a.

The subsequent step S45 serves to decide whether or not the selected examination management data has already been registered in the database 11. In a case where the data has not been registered yet, the selected examination management data is registered in (namely, added to) the database 11 as indicated at a step S46, whereupon the import process is ended. On the other hand, in a case where the selected examination management data has been already registered in the database 11, whether or not the data already registered in the database 11 is imported data is decided as indicated at a step S47. On condition that the data is the imported one, i.e., that the import flag 15b is "1" (ON), the examination management data loaded at the step S44 is overwritten into the database 11 as indicated at a step S48, whereupon the import process is ended. In addition, on condition that the data already registered in the database 11 is not the imported one, i.e., that the import flag 15b is "0" (OFF), the process is ended without rewriting the database 11, as indicated at a step S49.

Owing to the import function as stated above, in spite of the examination made on the side of the one image file apparatus 1a by way of example, the data concerning this examination can be utilized for search and reproduction by the other image file apparatus 1b.

When the import process of data has been executed in the above way, the data for the identical examination exists in the respective databases 11 of the plurality of image file apparatus 1a and 1b. On this occasion, when the data is modified and updated in one image file apparatus 1a, the match of the data is temporarily lost between the plurality of image file apparatus 1a and 1b. In the case where the match of the data has been temporarily lost in this manner, it can be recovered by the operational contrivance that the data modified and updated in one image file apparatus 1a is imported into the other image file apparatus 1b. However, when the same data has been submitted to different modifications in the plurality of image file apparatus 1a and 1b, which of the resulting data items has a proper content cannot be judged, and it is difficult to recover the match.

In this embodiment, therefore, only one image file apparatus 1a used in the examination is granted to modify and update the data, and the other image file apparatus 1b is inhibited from modifying and updating the pertinent data. That is, the data for which the import flag 15b is "1" (ON) is not allowed to be modified and updated, and it is used for reference only. Thus, it is avoided to incur the mismatch of data attributed to the modifications of the same data in the plurality of image file apparatus 1a, 1b. In addition, since the data for which the import flag 15b is "1" (OFF) is allowed to be modified and updated, the loss of the modified and undated data is avoided in such a way that, as indicated at the step S49, the import process for the pertinent data is cancelled. In addition, since the data for which the import flag 15b is "1" (ON) is not allowed to be modified and updated, it is always overwritten in the import process as indicated at the step S48, for which the generation of the data is updated to the newest one by the import process. That is, the match of the data between the plurality of image file apparatus 1a, 1b is ensured by the steps S47, S48 and S49.

According to this embodiment thus far described, the shared data including image data are stored in the external storage media such as MO media, and the information items of the association between the external storage media and the shared data are stored in the image file apparatus. Therefore, when the plurality of image file apparatus not connected to a network are used, the data are permitted to be shared between the image file apparatus.

In addition, unique storage medium identification information items are respectively assigned to the individual storage media in which the shared data are stored, and the association information items between the shared data and the storage medium identification information are stored in the individual image file apparatus. When the image file apparatus needs to load the shared data, it indicates the storage medium identification information and requests the operator to mount the external storage medium. Therefore, the operator can reliably select the desired external storage medium from among the plurality of external storage media and mount it in the image file apparatus.

Further, each of the storage medium identification information items assigned to the external storage media contains identification information unique to the facilities where the image file apparatus is disposed, identification information for specifying the image file apparatus in the identical facilities, and identification information for specifying the order of formats to which the external storage medium is submitted by the identical image file apparatus. Therefore, the same storage medium identification information is not assigned to different facilities, and the external storage medium can be reliably specified by the storage medium identification information.

By way of example, the external storage medium thirdly formatted by the second image file apparatus of a hospital A, and the external storage medium thirdly formatted by the second image file apparatus of a hospital B cannot be specified in a case where the identification information unique to the facilities is not contained in the storage medium identification information. In contrast, according to this embodiment, the external storage media can be identified because the identification information unique to the facilities is contained in the storage medium identification information.

Moreover, since the shared data loaded from the external storage medium into the storage means of the image file apparatus is not allowed to be modified and updated, the mismatch of the shared data between the image file apparatus is preventable because the shared data respectively stored in the storage means of the plurality of image file apparatus are differently modified and updated by the individual image file apparatus.

The present invention is not restricted to the foregoing embodiments only, but it can be variously altered within a scope not departing from the purport of the invention.

By way of example, it is a matter of course that image data to be stored in the image file apparatus need not be restricted to the image data generated by the endoscope unit.

It is obvious that different embodiments in a wide range can be constructed on the basis of the present invention without departing from the spirit and scope of the invention. The present invention is not limited by the embodiments thereof except being restricted by the appended claims.

What is claimed is:

1. An image file apparatus, comprising:
   a recording-medium mount for exchangeably mounting a first recording medium on which first image information can be recorded;
   an image-information recorder for recording the first image information on said first recording medium which can be mounted in said recording-medium mount;
   a managing-data creation unit for creating first managing data for said first image information which is recorded on said first recording medium by said image-information recorder;
   a database for storing therein the first managing data which is created by said managing-data creation unit;

a unit for additionally storing second managing data for second image information which is recorded on a second recording medium, in said database when said second recording medium on which the second image information not managed by said database is recorded is mounted in said recording-medium mount; and an image information searcher for searching image information which corresponds to said first or second managing data recorded in said database in said first or second recording-medium mounted in said recording-medium mount.

2. An image file apparatus according to claim 1, further comprising:

an identification-information assignment unit for assigning identification information unique to said first or second recording medium, on said first or second recording medium which can be mounted in said recording-medium mount;

wherein said managing-data creation unit creates said first managing data for said first image information which is recorded on said first recording medium, in association with the unique identification information assigned by said identification-information assignment unit; and said unit additionally stores the second managing data for the second image information which is recorded on the second recording medium, in said database in association with the unique identification information assigned by said identification-information assignment unit.

3. An image file apparatus according to claim 2, wherein said database identifies said first or second recording medium on the basis of said unique identification information assigned by said identification-information assignment unit, and in accordance with a result of the identification, it makes a request for a first or second storage medium in which desired image data is stored, in a case where the first or second storage medium storing the desired image data therein is not mounted in said recording-medium mount.

4. An image file apparatus according to claim 2, wherein said unique identification information assigned by said identification-information assignment unit is managed on the basis of information for managing image data as is included in said database.

5. An image file apparatus according to claim 3, wherein in a case where the request for said first or second storage medium storing said desired image data therein has been made by said database, the identification information of the desired first or second storage medium is displayed at a predetermined position of a display window which is displayed by a display.

6. An image file apparatus according to claim 1, wherein the first or second storage medium contains unique identification information items in an order in which it is formatted.

7. An image file apparatus according to claim 1, wherein said second managing data additionally stored in said database is inhibited from being edited.

8. An image file system, comprising:

a first image file apparatus which is provided with a first recording-medium mount for exchangeably mounting a first recording medium capable of recording first image information thereon;

a first image-information recorder provided in said first image file apparatus, for recording the first image information on the first recording medium which can be mounted in said first recording-medium mount;

a first managing-data creation unit provided in said first image file apparatus, for creating first managing data for said first image information which is recorded on said first recording medium by said first image-information recorder;

a managing-data recorder provided in said first image file apparatus, for recording on said first recording medium the first managing data which is created by said first managing-data creation unit;

a second image file apparatus which is provided with second recording-medium mount means for exchangeably mounting a second recording medium capable of recording second image information thereon;

a second image-information recorder provided in said second image file apparatus, for recording the second image information on the second recording medium which can be mounted in said second recording-medium mount;

a second managing-data creation unit provided in said second image file apparatus, for creating second managing data for said second image information which is recorded on said second recording medium by said second image-information recorder;

a database provided in said second image file apparatus, for storing therein the second managing data which is created by said second managing-data creation unit; and an additional-storage database provided in said second image file apparatus, for additionally storing the first managing data recorded on the first recording medium, in said database when said first recording medium on which the first image information is recorded in said first image file apparatus is mounted in said second recording-medium mount.

9. An image file system according to claim 8, further comprising:

an identification-information assignment unit for assigning identification information unique to an apparatus main body in the first and second image file apparatus, on said first image file apparatus furnished with the first recording medium which can be mounted in said first recording-medium mount, and on said second image file apparatus furnished with the second recording medium which can be mounted in said second recording-medium mount;

wherein said managing-data creation unit creates said first managing data for said image information which is recorded on said first recording medium, in association with the unique identification information assigned by said identification-information assignment unit; and said additional-storage database additionally stores the second managing data for the second image information which is recorded on said second recording medium, in said database in association with said unique identification information assigned by said identification-information assignment unit.

10. An image file system according to claim 9, wherein said database identifies said first and second image file apparatus on the basis of said identification information unique to the apparatus main body as is assigned by said identification-information assignment unit, and in accordance with a result of the identification, it makes a request for the second storage medium in which desired image data is stored, in a case where said second storage medium storing the desired image data therein is not mounted in said first recording-medium mount.

11. An image file apparatus according to claim 9, wherein said identification information unique to the apparatus main body as is assigned by said identification-information assignment unit is managed on the basis of information for managing image data as is included in said database.

12. An image file system according to claim 10, wherein in a case where the request for said second storage medium storing said desired image data therein has been made by said database, the identification information of said second storage medium is displayed at a predetermined position of a display window which is displayed by a display.

13. An image file system according to claim 8, wherein the first or second storage medium contains unique identification information items in an order in which it is formatted.

14. An image file system according to claim 8, wherein said second managing data additionally stored in said database is inhibited from being edited.

15. A database creating method in an image file apparatus, comprising:

- an image-information record step of recording first image information on a first recording medium which can be mounted in recording-medium mount, by an image-information recorder;
- a managing-data creation step of creating first managing data for the first image information which is recorded on said first recording medium by said image-information recorder;
- a database storage step of storing said first managing data which is created by said managing-data creation step, in a database;
- a database additional-storage step of additionally storing second managing data for second image information which is recorded on a second recording medium, in said database when said second recording medium on which the image information not managed by said database is recorded is mounted in said recording-medium mount; and
- an image-information searching step of searching image information which corresponds to said first or second managing data recorded in said database in said first or second recording medium mounted in said recording-medium mount.

16. A database creating method in an image file apparatus as defined in claim 15, further comprising:

- the identification-information assignment step of assigning identification information unique to said first or second recording medium, on said first or second recording medium which can be mounted in said recording-medium mount;
- wherein said managing-data creation step creates said first managing data for said first image information which is recorded on said first recording medium, in association with the unique identification information assigned by said identification-information assignment step; and
- said database additional-storage step additionally stores the second managing data for the second image information which is recorded on said second recording medium, in said database in association with said unique identification information assigned by said identification-information assignment step.

17. A database creating method in an image file apparatus as defined in claim 15, further comprising:

- the identification step of allowing said database to identify said first or second recording medium on the basis of said unique identification information assigned by said identification-information assignment step; and
- the request step of allowing said database to make a request in accordance with a result of the identification by said identification step, for the first or second storage medium in which desired image data is stored, in a case where said storage medium storing the desired image data therein is not mounted in said recording-medium mount.

18. A database creating method in an image file apparatus as defined in claim 15, further comprising the management step of managing said unique identification information assigned by said identification-information assignment step, on the basis of information for managing image data as is included in said database.

19. A database creating method in an image file apparatus as defined in claim 17, comprising displaying the identification information of the desired first or second storage medium at a predetermined position of a display window which is displayed by a display, in a case where the request for said first or second storage medium storing said desired image data therein has been made by said request step.

20. A database creating method in an image file apparatus as defined in claim 15, further comprising:

- the second image-information record step of recording second image information on a second recording medium which can be mounted in second recording-medium mount, said second image-information record step being executed by a second image file apparatus which is included in the first-mentioned image file apparatus;
- wherein said database storage step stores the second managing data created by said managing-data creation step, in a database of the second image file apparatus; and
- said database additional-storage step additionally stores said first managing data recorded on said first recording medium, in said database.

21. A database creating method in an image file apparatus as defined in claim 20, further comprising:

- the identification step of allowing said database to identify said second image file apparatus on the basis of the identification information unique to the apparatus main body as is assigned by said identification-information assignment step; and
- the request step of allowing said database to make a request in accordance with a result of the identification by said identification step, for the second storage medium in which desired image data is stored, in a case where the second storage medium storing the desired image data therein is not mounted in said first recording-medium mount.

22. A database creating method in an image file apparatus as defined in claim 20, further comprising the management step of managing the identification information unique to the apparatus main body as is assigned by said identification-information assignment step, on the basis of information for managing image data as is included in said database.

* * * * *